(12) United States Patent
Hennig et al.

(10) Patent No.: US 8,847,434 B2
(45) Date of Patent: Sep. 30, 2014

(54) ANTENNA ARRANGEMENT AND TRANSPONDER READER

(75) Inventors: Andreas Hennig, Muehlheim (DE); Gerd Vom Boegel, Wuelfrath (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 615 days.

(21) Appl. No.: 13/023,577

(22) Filed: Feb. 9, 2011

(65) Prior Publication Data

US 2011/0193418 A1 Aug. 11, 2011

(30) Foreign Application Priority Data

Feb. 10, 2010 (EP) .................................. 10001367
May 14, 2010 (DE) ......................... 10 2010 028 993

(51) Int. Cl.

| | | |
|---|---|---|
| H01F 27/42 | (2006.01) | |
| H01Q 21/28 | (2006.01) | |
| A61B 5/00 | (2006.01) | |
| A61B 5/07 | (2006.01) | |
| H01Q 1/52 | (2006.01) | |
| H01Q 1/22 | (2006.01) | |

(52) U.S. Cl.
CPC ............... *A61B 5/076* (2013.01); *H01Q 21/28* (2013.01); *A61B 5/0031* (2013.01); *H01Q 1/525* (2013.01); *H01Q 1/2216* (2013.01)
USPC ...................................................... 307/104

(58) Field of Classification Search
CPC ...................................................... H01F 27/42
USPC ...................................................... 307/104
See application file for complete search history.

(56) References Cited

U.S. PATENT DOCUMENTS

| | | | |
|---|---|---|---|
| 2,887,650 A | | 5/1959 | Ruddock et al. |
| 3,576,495 A | * | 4/1971 | Yoshizato .................. 455/193.1 |
| 3,614,600 A | | 10/1971 | Ronka et al. |
| 5,541,604 A | | 7/1996 | Meier |
| 7,079,084 B2 | | 7/2006 | Notohara et al. |

(Continued)

FOREIGN PATENT DOCUMENTS

| | | |
|---|---|---|
| DE | 694 23 474 T2 | 9/2000 |
| DE | 11 2004 002 040 T5 | 9/2006 |

(Continued)

OTHER PUBLICATIONS

Jung et al., "A Dual Band Wireless Power and FSK Data Telemetry for Biomedical Implants", Proceedings of the 29th Annual International Conference of the IEEE EMBS, Aug. 23-26, 2007, pp. 6596-6599.

(Continued)

*Primary Examiner* — Dameon E Levi
*Assistant Examiner* — Andrea Lindgren Baltzel
(74) *Attorney, Agent, or Firm* — Keating & Bennett, LLP

(57) ABSTRACT

An antenna arrangement has an inductive transmitting antenna having a main radiating axis, an inductive receiving antenna having a main receiving axis, and an inductive compensator. The inductive receiving antenna is arranged in the main radiating axis of the transmitting antenna. The inductive compensator is electrically connected in series to the receiving antenna and is arranged in a first plane which intersects a second plane. The main receiving axis of the receiving antenna here is normal to the second plane.

15 Claims, 19 Drawing Sheets

(56) References Cited

U.S. PATENT DOCUMENTS

| | | | |
|---|---|---|---|
| 2005/0029919 A1 | | 2/2005 | Notohara et al. |
| 2005/0104781 A1 | | 5/2005 | Notohara et al. |
| 2005/0154428 A1 | * | 7/2005 | Bruinsma ................ 607/60 |
| 2009/0026266 A1 | | 1/2009 | Raggam |
| 2009/0134711 A1 | * | 5/2009 | Issa et al. ................ 307/104 |
| 2009/0195366 A1 | | 8/2009 | Meier et al. |
| 2009/0309578 A1 | * | 12/2009 | Cochran ................ 324/207.16 |

FOREIGN PATENT DOCUMENTS

| | | |
|---|---|---|
| DE | 10 2007 019 672 A1 | 8/2008 |
| DE | 10 2008 034 001 A1 | 1/2009 |
| DE | 10 2007 049 486 A1 | 4/2009 |
| EP | 1 696 362 B1 | 7/2008 |

OTHER PUBLICATIONS

Finkenzeller, "RFID Handbook", 1999, Wiley & Sons Ltd, 11 pages.

Hennig et al., "Passive Transponder for an RFID System, and Method of Transmitting Data From/to a Data Source of Such a Passive Transponder", U.S. Appl. No. 12/958,612, filed Dec. 2, 2010.

Henning et al., "Antenna Device, Transponder Reader, Induction Cooker," U.S. Appl. No. 13/107,033, filed May 13, 2011.

\* cited by examiner

ANTENNA ARRANGEMENT AND TRANSPONDER READER

CROSS-REFERENCE TO RELATED APPLICATIONS

This application claims priority from European Patent Application No. 10001367.1, filed Feb. 10, 2010, and from German Patent Application No. 102010028993.0, filed May 14, 2010, which are both incorporated herein by reference in their entirety.

BACKGROUND OF THE INVENTION

Embodiments of the present invention describe an antenna arrangement as may exemplarily be used in a transponder reader, such as, for example, an RFID (radio frequency identification) reader or NFC (near field communication) reader. Further embodiments of the present invention describe a transponder reader, such as, for example, an RFID reader or NFC reader.

The use of transponder technologies particularly in medical applications opens valuable possibilities in therapy of human cardiovascular system diseases, for example cardiac insufficiency. Especially for applications where a transponder is coupled with a sensor to be deeply implanted into human body, several requirements have to be kept in mind. These are, for example, a high transmission range and at the same time small transponder antenna dimensions. At present, there are no systems that meet these requirements.

Transponders with attached sensors are of particular interest in medical applications. Implanted inside the human body, such transponders can measure particularly blood pressure and temperature, to improve the therapy of cardiovascular diseases. Especially passive transponders are of interest, because they do not need any power supply in form of a local battery. Thus passive transponders can stay inside the human body for a long time. To make catheter implantation possible, the dimensions of a transponder antenna (loop, coil) are limited to about 2 mm×8 mm (diameter×length).

FIG. 5 shows such a sensor transponder system consisting of a transponder reader 10 and a transponder 20. The transponder reader 10 here is typically located outside the human body so as to read the transponder 20 placed inside the human body. Using its antenna 12, the transponder reader 10 generates a magnetic field which is received by the antenna 22 of the transponder 20 and induces a voltage which is made use of for supplying the transponder 20. The transponder 20 responds to the magnetic field emitted by the transponder reader 10 by so-called load modulation, i.e. by connecting and disconnecting the resistor R of the transponder 20, a current flow $I_T$ of the transponder 20 can be changed, thereby loading a magnetic field 23 emitted by the transponder reader 10, which is detected by a receiver 24 of the transponder reader 10 and converted to data.

In addition, electrical losses occur during transmission through body tissues. This fact and the small dimensions of the transponder antenna 22 reduce the so-called mutual inductance between the antenna 22 of the transponder 20 and the antenna of an external device (of the transponder reader 10, usually also referred to as reader) which is able to transmit power supply signals to the transponder 20 and to also receive data transmitted by the transponder 20.

In addition, electrical losses occur during transmission through human tissue. These facts reduce the so-called mutual inductance between the antenna of the transponder and the antenna of an external device (usually called reader) which is able to transmit powering signals to the transponder as well as to receive data which are transmitted by the transponder.

It has to be mentioned that the transmission mechanism used in transponder technology under consideration is typically based on the magnetic coupling of a transmitting antenna loop (e.g. a coil with one or more windings) and a receiving antenna loop (or coil of a transponder, as mentioned) by a magnetic field of the transmitting antenna loop.

This means that the mutual inductance is a measure of the magnetic coupling of the reader and the transponder antenna (loop). In consequence, the maximum possible distance is reduced. For this application in implantable transponders, the bridgeable distance has to be up to 40 cm. To reach this range, optimized antennas and high transmission power are needed. It was shown that a frequency of 6.78 MHz for transmitting powering radiation and receiving data achieves best results in this application. But a frequency of 13.56 MHz achieves acceptable results as well. To provide sufficient energy to the transponder chip over this distance, the voltage amplitude over the reader antenna loop or coil in the relevant system under consideration may be in the range of 240V and more.

Especially in medical applications a sensor transponder should measure a number of physical parameters, such as blood pressure, temperature and also the supply voltage inside the transponder. To make medical diagnostics possible, the pressure history of heart beats has to be transmitted in the resolution needed. Protocol complexity has to be regarded, too.

Moreover, in some sensor transponders parallel measurement and data transmission is not possible because of power limitations. A data rate of 13 kBit/s should be assumed below. It follows that the transmission channel has to have a minimum bandwidth of 26 kHz, using a load-modulation technique.

In some passive transponder systems, load modulation is used to transmit data from the transponder to a reader. Thereby, the impedance of the transponder is changed to modulate a carrier that is produced by the reader. The transponder is provided with energy by this carrier signal. Energy and data transmission are coupled processes. This is one of the disadvantages of this wide-spread technique. To enlarge the energy range, the quality factor of the antennas in the system has to be increased. On the other hand, antennas with high quality factors have low bandwidths. Hence the data rate is limited. Moreover the signal to noise ratio (SNR) and the signal to carrier ratio (SCR) are low in this case. In transponder techniques this problem is called the "quality-bandwidth dilemma". Especially in medical applications, high transmission range and continuous pressure value transmission (for example of blood pressure) are needed. Calculations in the next section show that these requirements cannot be fulfilled at the same time when using a conventional reader antenna coil.

Analysis of the Transmission Channel
—Transfer Function

The transfer function is needed to analyze the behavior of the transmission channel. For example expectable signal strength and frequency characteristics can be found out. To derive a transfer function the equivalent circuit shown in FIG. 6 is used. It is based on the technical circuit shown in FIG. 5.

The variation of the voltage over the resonant circuit caused by the modulation resistor R can be modulated by a voltage source $V_T$. The transmission channel itself is represented by a transformer equivalent circuit. Losses are represented by $R_R$ and $R_T$. The generator is represented by its inner resistance $R_G$. The transfer function $V_C/V_T$ can be derived by solving Kirchhoff's mesh-law. The result is a first order bandpass function. Using the following parameters the transfer function for this application could be derived. The parameters of a typical arrangement are $L_R$=409 nH, $R_R$=9.8 mΩ, C=1.1 nF, $R_T$=2.4Ω.

The transfer function (based on the assumed parameters) is shown in FIG. 7. By switching the load resistor R, an amplitude variation of the carrier is produced. In the frequency domain, upper- and lower-sidebands appear. The generator signal, transmitted from the reader to the transponder, acts as a carrier for data transmission in the opposite direction.

A 13 kBit/s Manchester coded signal has baseband frequency components at 26 kHz. At the corresponding sideband frequencies, the transfer ratio is about 0.000196. In case of a modulation voltage of 1 V at the transponder side about 200 µV is reached at the reader antenna. In comparison to the sensitivity of common receivers that is about 1 µV, this value is high enough. Sensitivity is no limitation here.

—Signal-to-Carrier Ratio

Usually, transponder systems feature the disadvantage that the received transponder signal is small compared to the transmitted signal, also called carrier signal. This makes signal processing in the reader difficult. High dynamic ranges and low-noise components are needed to enable detection of the transponder. So the so-called signal-to-carrier ratio is of interest to describe the relevant properties of the system. As mentioned before, in such kind of application a voltage amplitude of about 240 V over the reader (=transmitter) antenna coil is needed to provide enough energy to the transponder in a distance of about 40 cm.

Hence the modulation index has a value of:

$$m = \frac{V_S}{V_C} \approx 8.34 \times 10^{-9} \%$$

This value is unfeasible low. To render this value better to detect, a signal-to-carrier ratio (SCR) can be defined by:

$$SCR = 10 \log \frac{V_{S-\mathit{eff}}^2}{V_{C-\mathit{eff}}^2} = 10 \log \frac{(140 \, \mu V)^2}{(170 \, V)^2} \approx -121.6 \, dB$$

To make such a signal processable, a sufficient amount of carrier suppression is needed.

—Bandwidth

As mentioned before, in the described example a minimum bandwidth of 26 kHz is needed. By evaluating the transfer function shown in FIG. 7 it can be seen that a baseband bandwidth of about 12 kHz is available here. If the signal was transmitted over such a narrow channel, inter-symbol interference would arise. In this case, a transmitted symbol influences the following symbols during a transmission. This fact makes decoding in the reader difficult or impossible.

—Detuning

Detuning of the reader antenna 12 causes a displacement of the transfer function in the frequency domain. Such a detuning could particularly also be caused by changing the distance between the antennas. As can be seen in FIG. 7, for a higher mutual inductance, the transfer function is shifted to higher frequencies. Because the demodulation is usually done synchronously to the generator signal, the shift also appears in the baseband. In consequence the baseband transfer function is no longer a first order low pass. In other words, the transponder signal is distorted. This effect is noticeable by a beat of the transponder signal. The beat frequency correlates to the detuning.

If the transponder is implanted near to the heart, it will move in rhythm with the heart beat. The mutual inductance depends on the orientation of the coils to each other. Because of that, the damping of the voltage over the reader antenna 12 will vary as well. This variation is noticeable in the baseband signal as a beat which covers the transponder signal.

—Noise

Several noise sources exist in a transponder system. The transponder signal is covered (or disturbed) by these noise voltages and currents. The noise sources are in the frequency generator, the power amplifier, the antenna and in the receiver.

Power amplifier noise consists of shot noise caused by PN junctions and Johnson-noise caused by resistors. Thus, the mean square voltage at the receiver is of interest. The mean square voltage produced by a conventional power amplifier (typical noise figure 16 dB) was measured as 2.3 mV. The gain of the parallel resonant antenna circuit causes an amplification of noise near to the resonant frequency.

With a receiver bandwidth of e.g. 100 kHz, which is needed for a 13 kBit/s Manchester coded signal, a mean square noise voltage of about 115 mV is reached. This value is several orders of magnitude higher than the transponder signal voltage, which is about 200 µV.

One could say that the power amplifier is the dominating noise source in the system and determines the SNR.

The SNR is a measure that describes the quality of the signal. If conventional load modulation is used, it can be calculated as follows:

$$SNR = 10 \log \frac{V_{S-\mathit{eff}}}{V_{noise}} = 10 \log \frac{(141 \, \mu V)^2}{(115 \, mV)^2} = -58.2 \, dB$$

For the described example a Manchester coded signal with 13 kBit/s is assumed. Usually an SNR of about +10 dB after filtering is needed to get an acceptable BER (bit error rate). This means that data transmission with conventional known antenna coils is not possible here.

Conventional Carrier Suppression Methods

Some known solutions try to overcome this problem. The three most frequently used solutions are presented as follows. However, it will be shown that all these solutions are unsuitable for an application over wider distances (as supposed in the examples).

The existing solutions can be divided into two groups:
techniques using carrier suppression circuit design, and
techniques using special antenna coil arrangement
to achieve carrier suppression.

One possible circuit design solution is using ceramic filters. Like shown in FIG. 8 one side-band 25 could be filtered and another side-band 27 be transmitted. The carrier signal 26 which is located outside the pass-band of the filter is suppressed. This method has several disadvantages. The dynamic range of active elements, like amplifiers, is usually not high enough. Hence, this solution could not be used alone. Only the side-band 27 can be used. Thus, half of the signal energy is lost. Further the bandwidth is still limited by the reader antenna coil. A sub-carrier would enlarge the spectral distance between the carrier 26 and the side-bands 25, 27 and implicate a better SNR. In this case, the data signal is multiplied by a periodic square wave function of constant frequency. Filtering would than be easier. Because of the bandwidth limitation this technique cannot be used in applications considered here (load modulation and medical applications of high data rates).

Beside circuit design solutions, it is possible to realize carrier suppression with the help of a special antenna (loop or coil) arrangement. To make this possible, a separate receiving antenna coil is used in the reader. Now the reader antenna arrangement consists of at least two loops or coils: at least one transmitting loop 12 or coil for energy transmission to the transponder and at least one receiving loop 31 or coil to receive the transponder signal. One possibility to improve the SCR and SNR is a spatial separation of transmitting 12 and receiving 31 coil(s). For example is it possible to place the receiving coil 31 on an opposite position to the transmitting coil 12 as shown in FIG. 9. The SCR is improved because the receiving coil 31 has less distance to the transponder coil 22 than to the transmitting coil 12. Spatial separation causes smaller coupling between the receiver coil 31 and the transmitting coil 12. However, this antenna arrangement is not feasible in most applications.

Additionally, DE 102008034001 A1 shows a pair of coils, including carrier suppression, which comprise a transmission coil and a reception coil. The transmission coil is configured to transmit a transmission signal which comprises a carrier. The reception coil is configured to receive a reception signal which comprises the carrier and data from a source and to suppress the carrier considerably and thus maintain coupling to the source in any position along and any position in proximity to the reception coil.

SUMMARY

According to an embodiment, an antenna arrangement may have: an inductive transmitting antenna having a main radiating axis; an inductive receiving antenna having a main receiving axis located in the main radiating axis of the transmitting antenna; inductive compensation means which is electrically connected in series to the receiving antenna and located in a first plane which intersects a second plane, the main receiving axis of the receiving antenna being normal to the second plane.

Another embodiment may have a transponder reader having an antenna arrangement as mentioned above.

Embodiments of the present invention provide an antenna arrangement comprising an inductive transmitting antenna, an inductive receiving antenna and inductive compensation means. The transmitting antenna comprises a main radiating direction or main radiating axis in which the receiving antenna is arranged. The receiving antenna comprises a main receiving direction or main receiving axis. The compensation means is connected in series to the receiving antenna and arranged in a first plane which intersects a second plane to which the main receiving direction of the receiving antenna is normal.

A core idea of the present invention is that an improved concept for carrier suppression in wireless communication systems can be provided when an antenna arrangement, in addition to a transmitting antenna and a receiving antenna, comprises compensation means which is arranged such that a magnetic field generated by the transmitting antenna causes, in the compensation means, a current which is opposite to a current caused by the magnetic field in the receiving antenna, so as to compensate (or largely compensate) the current induced in the receiving antenna, but that a magnetic field originating from a transponder located in the magnetic field of the transmitting antenna does not induce a current (or only a negligible current) in the compensation means so that the magnetic field originating from the transponder is not compensated by the compensation means. It has been recognized that the magnetic field of the transmitting antenna is circular around the transmitting antenna in direct proximity to the transmitting antenna, whereas the magnetic field of the transponder which is at a certain distance from the transmitting antenna and the receiving antenna, at the receiving antenna, when placing the transponder in the main radiating direction of the transmitting antenna and/or the main receiving direction of the receiving antenna, is nearly parallel to the main radiating direction of the transmitting antenna and/or the main receiving direction of the receiving antenna. This means that the magnetic field of the transponder does not generate an induced current (or only negligible induced current) in the compensation means, but does generate an induced (and detectable) current in the receiving antenna.

Consequently, an advantage of embodiments of the present invention is that they allow a magnetic field emitted by a transmitting antenna to be suppressed in a receiving antenna and at the same time a magnetic field emitted by a transponder not to be compensated. This results in an increased sensitivity of embodiments of the present invention compared to antenna arrangements which do not comprise compensation means arranged in a plane which is anti-parallel to a main radiating direction of the transmitting antenna of the antenna arrangement.

BRIEF DESCRIPTION OF THE DRAWINGS

Embodiments of the present invention will be detailed subsequently referring to the appended drawings, in which.

DETAILED DESCRIPTION OF THE INVENTION

Figure 1:
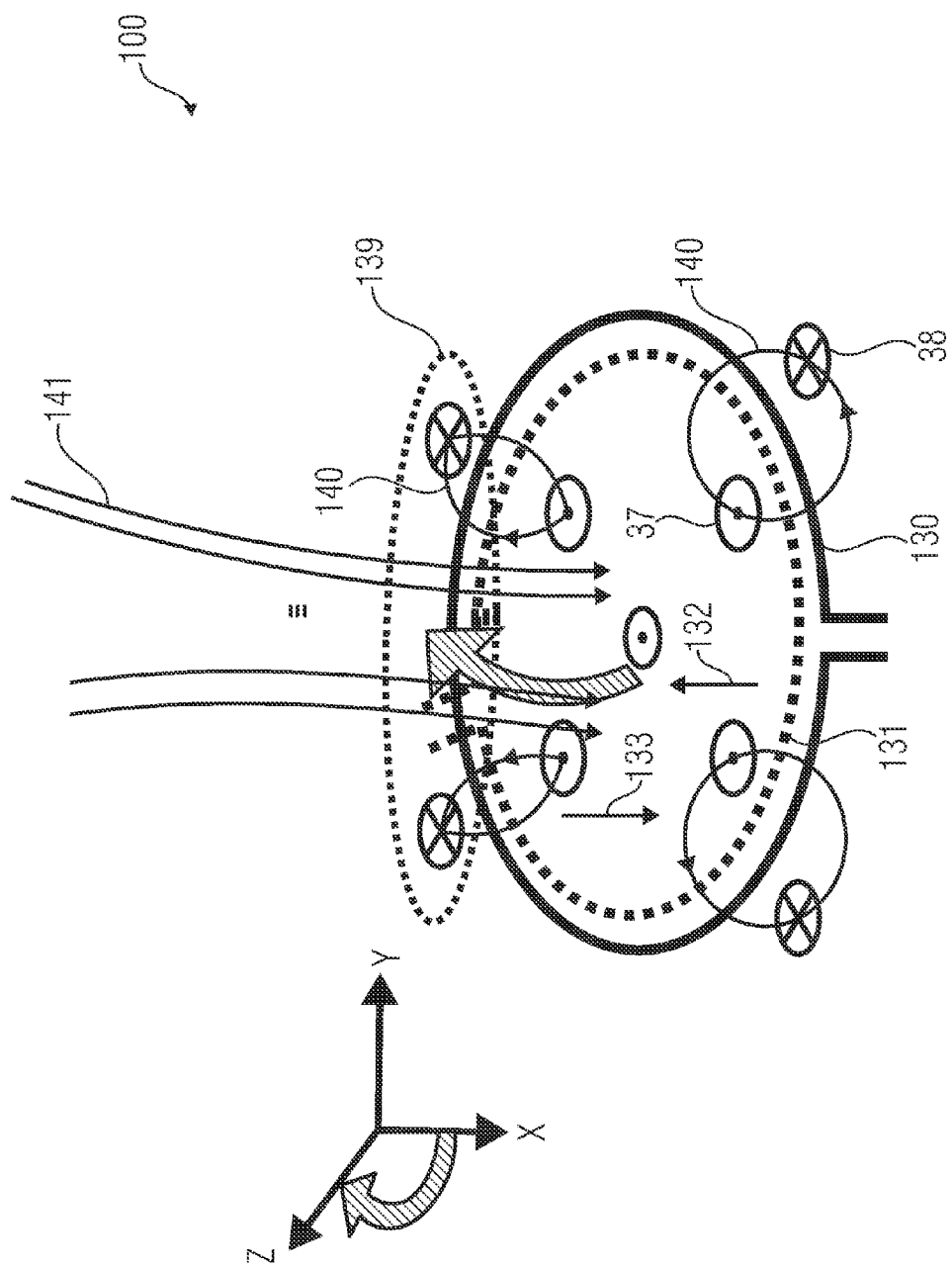
FIG. 1 shows a schematic illustration of an antenna arrangement in accordance with an embodiment of the present invention.

Before embodiments of the present invention are detailed below making reference to the enclosed figures, it is to be pointed out that same elements or elements of equal function are provided with the same reference numerals in the figures and that a repeated description of these elements is omitted. It follows that descriptions of elements having same reference numerals may be exchanged mutually or apply correspondingly.

An approach of how to arrive at the present invention will be described below making reference to FIGS. 10-13. After that, embodiments of the present invention will be described making reference to FIGS. 1-4.

A transmitting antenna may subsequently also be referred to as a transmitting coil, transmitter coil or transmitting loop. A receiving antenna may subsequently also be referred to as a receiving coil, receiver coil or receiving loop. A transmitting antenna and a receiving antenna here each comprise at least one winding.

Figure 10:
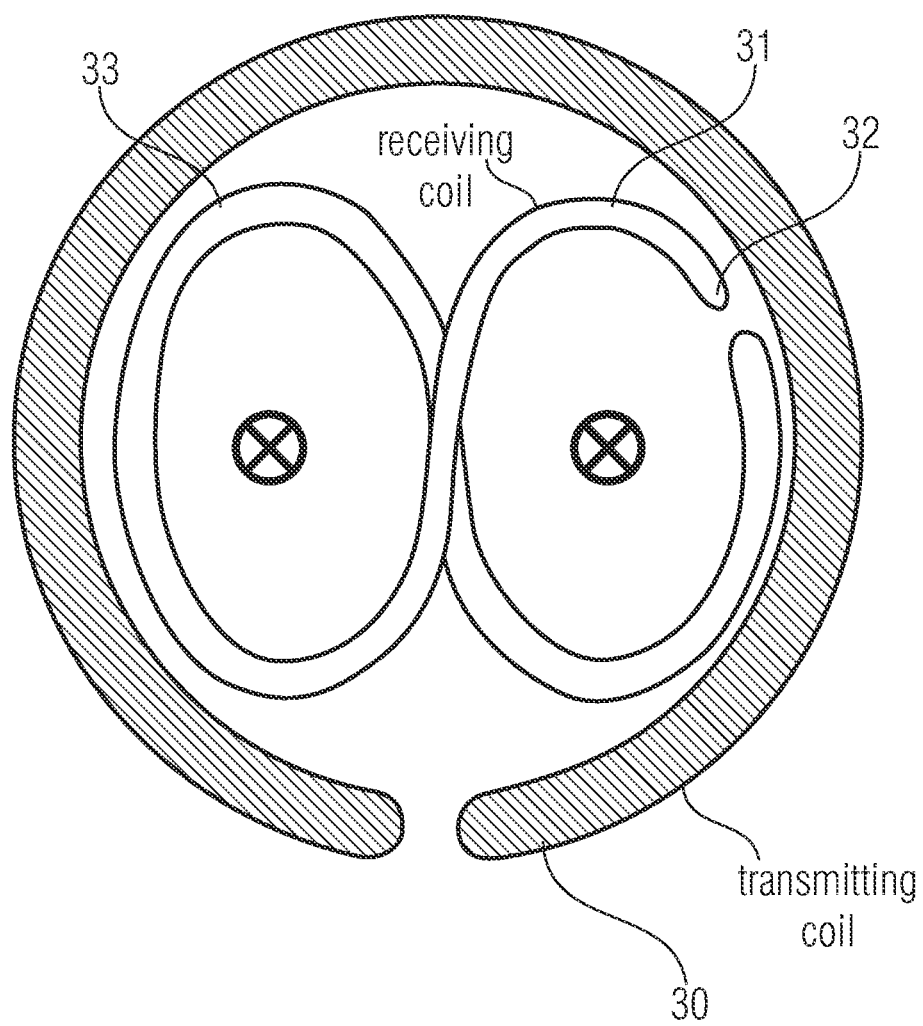
FIG. 10 shows a schematic illustration of a coil arrangement.

Because of the disadvantages of the concepts described in the introductory part, the following solution was developed: First FIG. 10 shows a possible arrangement of transmitting 30 and receiving 31 coils. In the example shown in FIG. 10, the receiving coil 31 is implemented in form of a "lying eight", so that one half 32 of the coil area of the receiving coil 31 has an opposite orientation in relation to another half 33 of the coil area of the receiving coil 31 and, more important, also to the transmitting coil 30. In this manner, the effect of the field lines generated by the transmitting coil 30 penetrating the receiver antenna 31 is compensated and, more precisely, no voltage is induced in the receiving coil 31. In other words, the receiver coil 31 is decoupled (in first order consideration) from the transmitting coil 30.

A transponder used in connection with the antenna arrangement shown in FIG. 10 is able to induce a voltage (in the receiving coil 31), but only if it is located over one half (either over half 32 or half 33) of the receiving coil 31. This is a decisive disadvantage of this solution. If the transponder is located in the middle of this antenna arrangement, it could not be read, because the compensation effect (caused by the opposite orientation of the two halves of the receiving coil 31) also occurs concerning the (magnetic) field generated by the transponder. This is disturbing in most applications and may be a criterion of exclusion for the antenna arrangement shown in FIG. 10.

Figure 11:
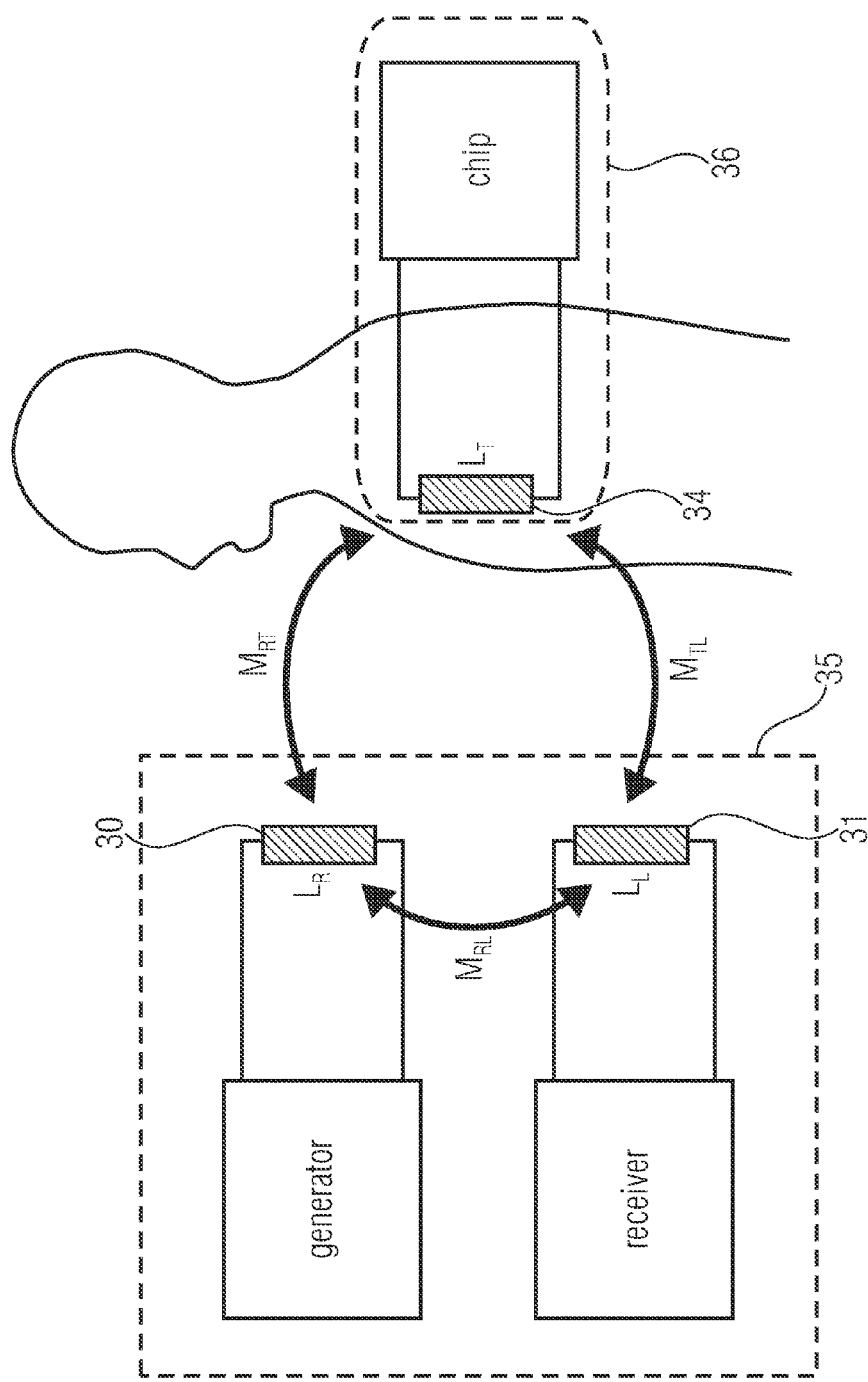
FIG. 11 shows a schematic illustration of coil coupling in a sensor transponder system.

FIG. 11 shows an approach which is based on the idea of enhancing the performance of the antenna arrangement with a separate receiving loop 31 or a receiving coil. Such a receiving loop 31 or receiving coil should be designed in such a way that it only receives signals transmitted by a transponder 36 (or modulated by same). The unwanted carrier signal (generated by a transmitting coil 30) should not be receivable (at least to a large extent) by this receiving loop 31 or coil. Moreover, the receiving coil 31 should have a maximum possible coupling to the transponder 36 located in the middle over the antenna setup (formed of the transmitting coil 31 and the receiving coil 31). In FIG. 11 which illustrates the approach three antenna loops or coils can be seen: A carrier transmitting loop or coil or transmitting coil 30 (in FIG. 11 also characterized by $L_R$) with a generator connected to a transponder antenna (in FIG. 11 also characterized by $L_T$) and the receiving loop or coil 31 (in FIG. 11 also characterized by $L_L$). The generator and the transmitting coil 30 and the receiver and the receiving coil 31 may exemplarily be located in a transponder reader 35. The aim of the arrangement shown in FIG. 11 is to keep the magnetic coupling $M_{TL}$ between the transponder 36 and the receiving coil 31 maximal and to keep at the same time the magnetic coupling $M_{RL}$ between the receiving coil 31 and the transmitting coil 30 minimal. This can be achieved by a "smart" spatial alignment of the antennas (of the individual coils). The requirements are: magnetically de-coupling of receiving coil 31 and transmitting coil 30 (at least to a large extent) and at the same time (nearly) unrestricted coupling of the receiving coil 31 to the transponder antenna 34. Moreover, the area where a transponder (the transponder 36) may be read should be in every position in front of the antenna arrangement.

Embodiments as are still to be described below meet all these requirements. To make this clear, the approach will be derived in several steps.

According to the second Maxwell Law, the voltage induced in a receiving loop or coil is proportional to the change of magnetic flux enclosed by the loop or coil area with respect to time:

$$\oint_S \vec{E} \cdot d\vec{s} = -\frac{d}{dt} \int_A \vec{B} \cdot d\vec{a}$$

"S" means the path along the loop or coil, A the area of the loop or coil and "B" the carrier field.

Figure 12:
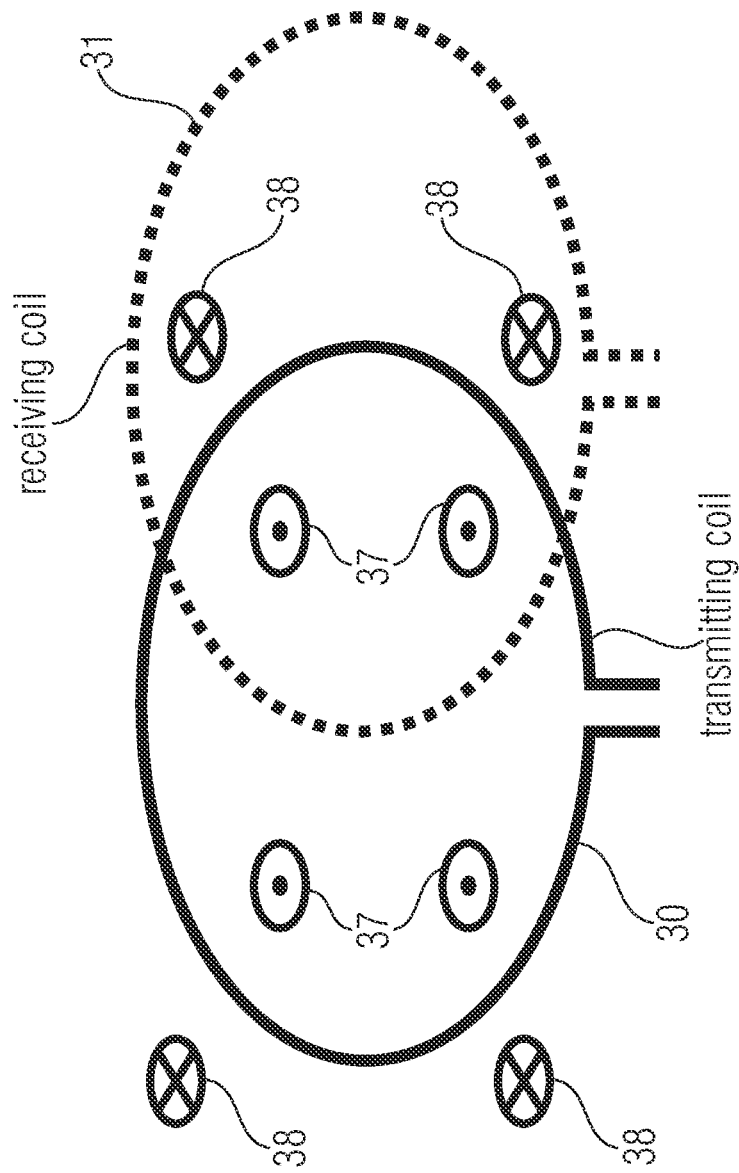
FIG. 12 shows a coil arrangement including offset receiving and transmitting coils.

FIG. 12 shows an antenna arrangement comprising a transmitting coil 30 and a receiving coil 31, the transmitting coil 30 and the receiving coil 31 being partly overlapping, but arranged offset from each other such that a main sensitivity area of the receiving coil 31 differs from a main radiating area of the transmitting coil 30. An orientation of the magnetic flux generated by the transmitting coil 30 is shown by markers 37 and 38. Marker 37 (illustrated as a circle with a point) indicates that the magnetic flux is out of the paper on which the antenna arrangement is drawn. Marker 38 (illustrated by a circle with a cross) indicates that the magnetic flux at this position is into the paper on which the antenna arrangement is drawn. It becomes evident from this that field lines which describe the magnetic flux are in opposite directions within and outside the area of the transmitting coil 30. The receiving coil 31 is arranged such that the field lines penetrating the area of the receiving coil 31 compensate each other. Thus, the carrier field generated by the transmitting coil 30 is compensated in the receiving coil 31.

But the optimal position for a transponder is in the middle over the coil area (both in the middle over the coil area of the transmitting coil 30 and in the middle over the coil area of the receiving coil 31), and thus it is not possible in the antenna arrangement shown in FIG. 12 to have optimum coupling to both coils (both the transmitting coil 30 and the receiving coil 31) at the same time in this solution.

Figure 13:
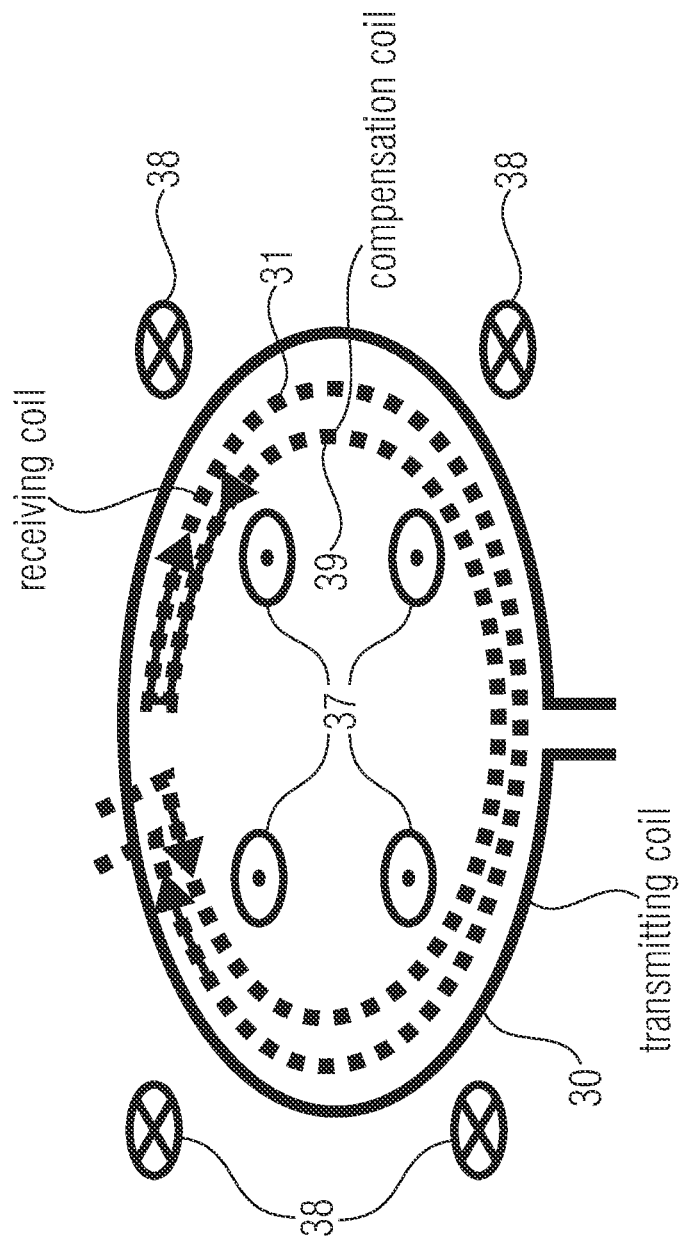
FIG. 13 shows a coil arrangement including a transmitting coil, a receiving coil and a compensation coil.

In another step shown in FIG. 13, the receiving loop or receiving coil 31 is divided into two sections. Both sections have the same coil area and each section is positioned inside the coil area of the transmitting coil 30. An inner section of the receiving coil 31 may also be referred to as a compensation coil 39. The two sections of the receiving loop or coil 31 are connected in series in such a way that all voltages induced by the carrier field (generated by the transmitting coil 30) in a section of the receiving coil 31 produce voltages of opposite polarity in the other section of the receiving coil 31. The carrier field of the transmitting coil 30 is also compensated by the opposite voltages in the two sections of the receiving coil 31. A disadvantage of the arrangement shown in FIG. 13, however, is that the field of a transponder which is placed over this setup would also be compensated. Transponder readout would not be possible in this case.

To prevent this, in embodiments of the present invention, one section (the compensation coil 39 shown in FIG. 13) of the receiving coil 31 is pivoted into a third plane (a plane differing from planes of the receiving coil 31 and the transmitting coil 30) which exemplarily is orthogonal to the other section of the receiving coil 31.

This is shown in FIG. 1 as a schematic illustration of an antenna arrangement 100 in accordance with an embodiment of the present invention. The antenna arrangement 100 comprises an inductive transmitting antenna 130 with a main radiating direction 132. Additionally, the antenna arrangement 100 comprises an inductive receiving antenna 131 with a main receiving direction 133, same being arranged in the main radiating direction 132 of the transmitting antenna 130. Additionally, the antenna arrangement 100 comprises inductive compensation means 139 which is electrically connected in series to the receiving antenna 131 and is arranged in a first plane which intersects a second plane, the main receiving direction 133 of the receiving antenna 131 being normal to this second plane.

As has already been mentioned before, the compensation means 139 (which may also be referred to as a compensation loop or compensation coil) may also be referred to as a second section of the receiving antenna 131 which is in a plane different from a first section of the receiving antenna 131. The main radiating direction or main radiating axis of the transmitting antenna 130 is that direction or axis in which a magnetic field (or carrier field) of the transmitting antenna 130 expands/propagates most strongly. Coupling between an antenna of a transponder and the transmitting antenna 130 will consequently be the highest if the transponder is arranged in the main radiating direction 132 of the transmitting antenna 130. A maximum distance between the transmitting antenna 130 and an antenna of a transponder can be achieved when the transponder (in the preferential direction or main radiating direction of its antenna) is arranged in the main radiating direction 132 of the transmitting antenna 130. The main radiating direction 132 of the transmitting antenna 130 here is typically perpendicular to a plane in which the transmitting antenna 130 is located.

In the embodiment shown in FIG. 1, the transmitting antenna 130 is located in the xy plane of a Cartesian coordinate system, whereby its main radiating direction 132 is along the z axis of the Cartesian coordinate system, which is perpendicular to the xy plane. The main receiving direction 133 of the receiving antenna 131 behaves in analogy to the main radiating direction 132 of the transmitting antenna 130, i.e. coupling between the receiving antenna 131 and an antenna of a transponder is at a maximum in the main receiving direction 133 or main receiving axis, and thus also a read range of the transponder. In the embodiment shown in FIG. 1, the receiving antenna 131 is arranged in the same xy plane as the transmitting antenna 130 or in a plane parallel thereto. The main receiving direction 132 of the receiving antenna 131 thus has the same course as the main radiating direction 132 of the transmitting antenna 130, along the z axis. The plane in which the receiving antenna 131 is thus forms the previously mentioned second plane to which the main receiving direction 133 of the receiving antenna 131 is normal. The first plane in which the compensation means 139 is located, in the embodiment shown in FIG. 1, is orthogonal to the second plane. This allows optimum suppression of the carrier field of the transmitting antenna 130, wherein a field of a transponder to be read out by the antenna arrangement 100 is not (or only slightly) compensated.

This is achieved by the fact that field lines 140 of a carrier magnetic field (so-called carrier field lines) are circular around a wire (or a conductor or a conductive trace or a bundle of wires) of the transmitting antenna 130 and thus penetrate the area of both sections of the receiving antenna 131. In other words, the carrier field lines 130 of the carrier field of the transmitting antenna 130 penetrate both the receiving antenna 131 and the compensation means 139. However, field lines 141 of a transponder only penetrate the first section of the receiving coil (only the receiving antenna 131), but not the second section of the receiving coil (not the compensation means 139). This means that the transponder field of the transponder is not (or only to an insignificant extent) influenced, as intended. As has already been mentioned, magnetic coupling to a coil of the transponder (to an antenna of the transponder) is optimal in this solution shown in FIG. 1 since the entire coil area of the transmitting antenna 130 (area spanned out by the transmitting antenna 130) is used by the receiving antenna 131 as well. The main radiating direction 132 of the transmitting antenna 130 is thus identical to the main receiving direction 133 of the receiving antenna 131 or is opposite in direction thereto.

In other words, embodiments of the present invention make use of the fact that field lines 140 of a carrier field and thus also the carrier field of a transmitting antenna 130 are circular around the transmitting antenna 130 at a short distance from the transmitting antenna 130 and that field lines 141 of a magnetic field of a transponder which is located in the carrier field of the transmitting antenna 130, at a certain distance from the transponder (i.e. in a receiving antenna 131), are nearly parallel and not circular. In the embodiment shown in FIG. 1, the field lines 141 of a transponder do cross the receiving antenna 131, but not the compensation means 139, thereby inducing a current in the receiving antenna 131, but not inducing a compensation current in the compensation coil 139. The field lines 140 of the carrier field of the transmitting antenna 130 in contrast cross both the receiving antenna 131 and the compensation means 139 (since they are circular around the transmitting antenna 130), thereby inducing a current in the receiving antenna 131 and inducing a compensation current in the compensation means 139. Thus, the compensation means 139 is connected in series to the receiving antenna 131 such that the current induced by the carrier field in the receiving antenna 131 (nearly) cancels out the compensation current induced by the carrier field in the compensation means 139. Embodiments of the present invention thus allow carrier suppression without influencing a magnetic field of a transponder (or only influencing same to an insignificant extent).

Although in the embodiment shown in FIG. 1 the first plane is orthogonal to the second plane and thus the compensation means 139 is orthogonal to the receiving antenna 131, in accordance with further embodiments, an angle between the first plane and the second plane may have any value greater than zero. This means that an angle between the first plane and the second plane may exemplarily be in a range from 45 degrees to 135 degrees, in a range from 65 degrees to 115 degrees, in a range from 80 degrees to 100 degrees or in a range from 85 degrees to 95 degrees. In addition, in accordance with further embodiments, the transmitting antenna 130 may be arranged in a plane which is anti-parallel to the second plane in which the receiving antenna 131 is located.

In accordance with some embodiments of the present invention, the transmitting antenna 130 and/or the receiving antenna 131 may comprise a winding or a plurality of windings. In addition, the transmitting antenna 130 and/or the receiving antenna 131 may comprise a conductor loop, exemplarily a circular conductor loop (as is shown in FIG. 1) or a rectangular conductor loop or a conductor loop of any shape. Such a conductor loop may exemplarily be realized by a wire or a plurality of wires or as a conductive trace or a plurality of conductive traces on a substrate.

Although in the embodiment shown in FIG. 1 the transmitting antenna 130 and the receiving antenna 131 are overlapping completely, in accordance with further embodiments, the transmitting antenna 130 and the receiving antenna 131 may overlap only partly.

Although in the embodiment shown in FIG. 1 the transmitting antenna 130 encloses the receiving antenna 131, in accordance with further embodiments, the receiving antenna 131 may also enclose the transmitting antenna 130.

As is shown in FIG. 1, the compensation means 139 may exemplarily be a conductor loop, exemplarily with one or several windings. A coil area of this conductor loop (area enclosed by the conductor loop) here is in a plane which is anti-parallel to the main receiving direction 133 of the receiving antenna 131.

It is pointed out that a radiating characteristic of a normal coil (as the transmitting antenna 130 and/or the receiving antenna 131 may exemplarily be) exhibits the shape of an eight, wherein the joint of such an eight is in that plane in which the windings of the coil are located.

In accordance with some embodiments of the present invention, a distance from the compensation means 139 to the transmitting antenna 130 may exemplarily be selected such that a field strength of a magnetic field originating from the transmitting antenna 130 is, at a position of the compensation means 139, still at least 90% of a maximum field strength of the magnetic field directly at the transmitting antenna 130. In accordance with one embodiment, the distance from the receiving antenna 131 to the transmitting antenna 130 may be selected to equal the distance from the compensation means 139 to the transmitting antenna 130 such that a magnitude of a field strength of the magnetic field of the transmitting antenna 130 at the receiving antenna 131 equals a magnitude of the field strength of the magnetic field of the transmitting antenna 130 at the compensation means 139 or differs therefrom by at most ±20%, at most ±15%, at most ±5% or at most ±1%.

Figure 2:
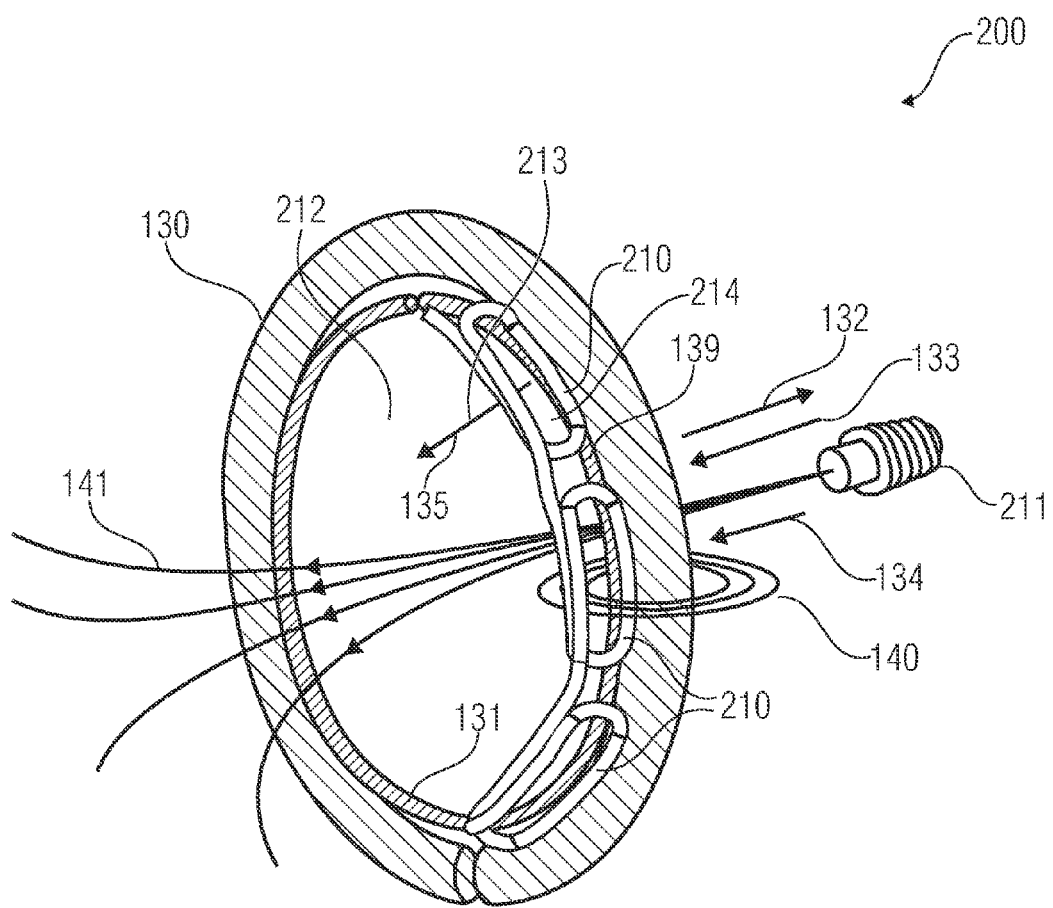
FIG. 2 shows a schematic illustration of an antenna arrangement in accordance with another embodiment of the present invention.

FIG. 2 shows an antenna arrangement 200 in accordance with another embodiment of the present invention. Here, too, the receiving antenna is divided into two sections. A first section is also referred to as receiving antenna 131 and the other (second) section as compensation means 139. The compensation means 139 may also be referred to as compensation coil 139. The compensation means 139 comprises a plurality of compensation coils 210 connected in series. In the embodiment in FIG. 2, the compensation means 139 comprises three compensation coils 210, each one of the compensation coils 210 comprising a winding. The transmitting antenna 130 and the receiving antenna 131 are each formed by a circular conductor loop. The compensation means 139 and, thus, the compensation coils 210 extend circularly along the conductor loop of the transmitting antenna 130 so that field lines 140 of the carrier field of the transmitting antenna 130 cross both a coil area 212 of the receiving antenna 131, a coil area 213 of the transmitting antenna 130 and a coil area 214 of the compensation coils 210. A coil area 212, 213 of the transmitting antenna 130 or the receiving antenna 131 here is that area spanned out by the respective conductor loop of the transmitting antenna 130 or the receiving antenna 131, or that area which it encloses. A coil area 214 of one of the compensation coils 210 here is that area spanned out by the windings of the compensation coil 210, or that area which the windings enclose. A magnetic field emanating from a transponder antenna 211 and thus the field lines 141 thereof, however, cross only coil area 213 of the transmitting antenna 130 and the coil area 212 of the receiving antenna 131 (due to the nearly parallel course of the field lines 141 at a certain distance from the transponder antenna 211). This means that none of the field lines 141 (or only a negligible portion of the field lines 141) of the magnetic field of the transponder antenna 211 crosses the coil areas 214 of the compensation coil 210 nor the compensation means 139. Like in the antenna arrangement 100 in accordance with FIG. 1 as well, in the antenna arrangement 200 the coil area 213 of the transmitting antenna 130 is also used by the receiving antenna 131, resulting in maximum coupling between both the transmitting antenna 130 and the transponder antenna 211 and between the receiving antenna 131 and the transponder antenna 211.

In the embodiment shown in FIG. 2, the transponder antenna 211 is located both in the main receiving direction 133 of the receiving antenna 131 and in the main radiating direction 132 of the transmitting antenna 130. Additionally, a main radiating direction 134 of the transponder antenna 211 is identical to the main receiving direction 133 of the receiving antenna 131 and the main radiating direction 132 of the transmitting antenna 130. A main receiving direction 135 of the compensation coils 210 here is perpendicular to the main radiating direction 134 of the transponder antenna 211, the magnetic field caused by the transponder antenna 211 (at a certain distance) not inducing a current (or only insignificantly little current) in the compensation means 139, i.e. in the compensation coils 210. The carrier field of the transmitting antenna 130, however, induces a current in both the receiving antenna 131 and in the compensation coils 210, since the field lines 140 of the carrier field are circular in direct proximity to the transmitting antenna 130 and the compensation means 139, and the compensation coils 210 of the compensation means 139, are arranged in direct proximity to the transmitting antenna 130. As described before, the compensation means 139 and, thus, its compensation coils 210 are connected such that a current induced in the compensation means 139, i.e. in the compensation coils 210, is opposite to a current induced in the receiving antenna 131 such that the current induced by the carrier field of the transmitting antenna 130 is cancelled out in the receiving antenna 131. A current in the receiving antenna 131 is caused only (or at least to a predominant extent) by the magnetic field generated by the transponder antenna 211.

Although in the embodiment shown in FIG. 2 only three compensation coils 210 are arranged in an area of the transmitting antenna 130, in accordance with further embodiments, the compensation means 139 may also comprise a greater or smaller number of compensation coils 210 which exemplarily extend along an entire area of the transmitting antenna 130 and exemplarily surround the coil area 213 of the transmitting antenna 130.

In practice, it is important to reduce the thickness of the antenna setup (of the antenna arrangement) 200 in order to arrive at a (nearly) planar realization. Therefore, and to avoid parasitic effects caused by asymmetry, in the antenna arrangement in FIG. 2, the compensation means 139 is built up by several small compensation coils 210 which are connected in series, the main area (the coil area 214) of these compensation coils 210 being orthogonal to the area of the transmitting coil area (the coil area 213 of the transmitting antenna 130) (i.e. pivoted in the first plane as has already been described in the previous embodiment). The compensation coils 210 here may be arranged to be symmetrical around the transmitting antenna 130.

In accordance with some embodiments of the present invention, the coil areas 214 of the compensation coils 210 and the number of windings of the compensation coils 210 can be selected such that the flux linkage caused by the carrier field is compensated. In other words, the coil areas 214 of the compensation coils 210 and the number of windings of the compensation coils 210 may be selected such that a magnitude of a compensation current generated by the carrier field of the transmitting antenna 130 in the compensation coils 210 equals a magnitude of a current induced by the carrier field of the transmitting antenna 130 in the receiving antenna 131.

Figure 3A:
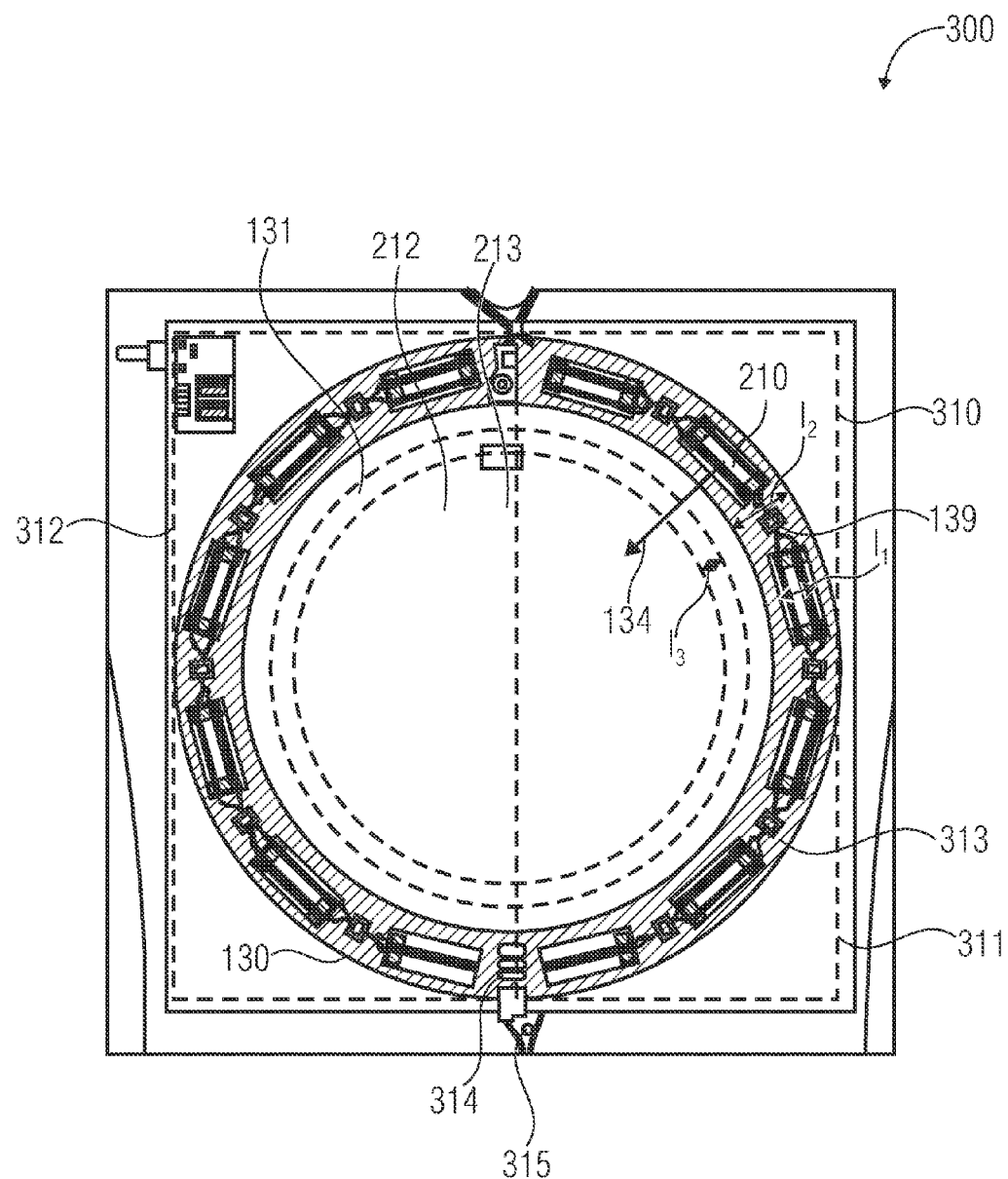
FIG. 3*a* shows a top view of an antenna arrangement in accordance with another embodiment of the present invention.

FIG. 3a shows an antenna arrangement 300 in accordance with another embodiment of the present invention Like in the previous embodiment, the antenna arrangement 300 also comprises an inductive transmitting antenna 130, an inductive receiving antenna 131 and inductive compensation means 139. The inductive compensation means comprises a plurality of compensation coils 210 (in the embodiment shown in FIG. 3a, 12 compensation coils 210) which are distributed along the transmitting antenna 130. The compensation coils 210 here are connected in series and each of the compensation coils 210 comprises at least one winding. These windings here are arranged in a first plane which intersects a second plane to which a main receiving direction of the receiving antenna 131 is orthogonal. In the specific embodiment shown in FIG. 3a, the first plane is orthogonal to the second plane and the receiving antenna 131 is located in the second plane. The transmitting antenna 130 is located in a third plane which is parallel to the second plane. In other words, like in the previous embodiment, a main radiating direction of the transmitting antenna 130 is identical to a main receiving direction of the receiving antenna 131. A main receiving direction 134 of the compensation coils 210 is orthogonal to both the main receiving direction of the receiving antenna 131 and the main radiating direction of the transmitting antenna 130. In other words, coil areas of the compensation coils 210 are orthogonal to a coil area 213 of the transmitting antenna 130 and to a coil area 212 of the receiving antenna 131.

In FIG. 3a, the receiving antenna 131 is indicated in broken lines since, as described before, it is located in a different plane than the transmitting antenna 130 which in this top view is into the plane of drawing below the plane of the transmitting antenna 130. In the embodiment shown in FIG. 3a, both the transmitting antenna 130 and the receiving antenna 131 and the compensation means 139 are arranged on a common substrate 310. The common substrate may exemplarily be a printed circuit board (PCB). A conductor 313 of the transmitting antenna 130 here may exemplarily be a conductive trace, exemplarily made of copper. In analogy, a conductor of the receiving antenna 131 may be another conductive trace (exemplarily made of copper) which is located in another layer of the substrate 310 (of the circuit board 310). The substrate 310 may exemplarily be a multi-layered conductor board, the transmitting antenna 130 being arranged on a first surface of the conductor board and the receiving antenna 131 being arranged on a second surface of the conductor board, opposite the first surface. In accordance with further embodiments, it may also be possible for both the transmitting antenna 130 and the receiving antenna 131 and the compensation means 139 to be arranged on the same surface of the conductor board.

In the embodiment shown in FIG. 3a, both the transmitting antenna 130 and the receiving antenna 131 are implemented to be circular conductor loops. In accordance with other embodiments, the conductor loops may be of any shape. In the embodiment shown in FIG. 3a, a diameter of the receiving antenna 131 is smaller than a diameter of the transmitting antenna 130, thus the transmitting antenna 130 encloses the receiving antenna 131. In accordance with further embodiments, a diameter of the receiving antenna 131 may be equal to or greater than the diameter of the transmitting antenna 130.

Additionally, the antenna arrangement 300 comprises tuning capacitors 314 which exemplarily serve for tuning the transmitting antenna 130 and/or the receiving antenna 131 to a desired resonance frequency.

In accordance with further embodiments, the antenna arrangement 300, as is shown in FIG. 3a, may comprise a feed terminal 315 which exemplarily serves for feeding an alternating voltage to the transmitting antenna 130 and/or for detecting a voltage induced in the receiving antenna 131.

As is also shown in FIG. 3a, an area of the transmitting antenna 130 may be divided into a first half 311 and a second half 312. Each of the compensation coils 210 of the compensation means 139 may be associated to precisely one of the two halves (either the first half 311 or the second half 312) of the transmitting antenna 130.

In accordance with further embodiments, compensation coils 210 which are associated to the first half 311 may be connected in series upstream of the receiving antenna 131 and compensation coils 210 which are associated to the second half 312 may be connected in series downstream of the receiving antenna 131. In the embodiment shown in FIG. 3a, six of the twelve compensation coils 210 are associated to the first half 311 and further six of the twelve compensation coils 210 of the compensation means 139 are associated to the second half 312. An exemplary antenna arrangement which is well suited for a frequency range of 6.28 MHz exemplarily has a diameter in a range of 20-30 cm and, advantageously, 26 cm and exhibits a thickness of less than 1 cm. As is shown in FIG. 3a, the antenna arrangement 300 and thus also the transmitting antenna 130 may be made of a printed circuit board (PCB) (which is also the substrate of the entire antenna arrangement 300). Thus, the antenna arrangement 300 is lightweight. Twelve compensation coils 210 orthogonal to the PCB plane are positioned to be in equal distances around the transmitting antenna 130 (on the conductor loop of the transmitting antenna 130). In accordance with some embodiments of the present invention, SMD (surface mounted device) coils may be used as compensation coils 210.

In accordance with some embodiments of the present invention, it is of advantage for the SMD coils (the compensation coils 210) to be of a length $l_1$ which is shorter than a width $l_2$ of the transmitting coil wire or the conductor loop 313 of the transmitting antenna 130. Thus, the carrier field of the transmitting antenna 130 penetrates all windings of the compensation coils 210. Additionally, it may be of advantage for a cross-section of the SMD coils (of the compensation coils 210) to be smaller in a height $h_1$ and larger in a width $b_1$ so as to keep the thickness of the setup (of the antenna arrangement 300) advantageously small.

A width of the conductor loop 313 of the transmitting antenna 130 may exemplarily be in a range of 10-60 mm, 20-40 mm, 25-35 mm or in a range of 30 mm±5%. A width $l_3$ of the conductor loop of the receiving antenna 131 may exemplarily be in a range between 0.01 mm to 10 mm, 0.02 mm to 5 mm, 0.05 mm to 1 mm or advantageously in a range of 0.1 mm±2%.

As has already been described above, windings of the compensation coils 210 may be dimensioned such that basically the same voltage is induced there by the carrier field of the transmitting antenna 130 as in the receiving antenna 131. Only then will the carrier signal be compensated optimally by the series connection of the compensation means 139 and the receiving antenna 131.

Figure 3B:
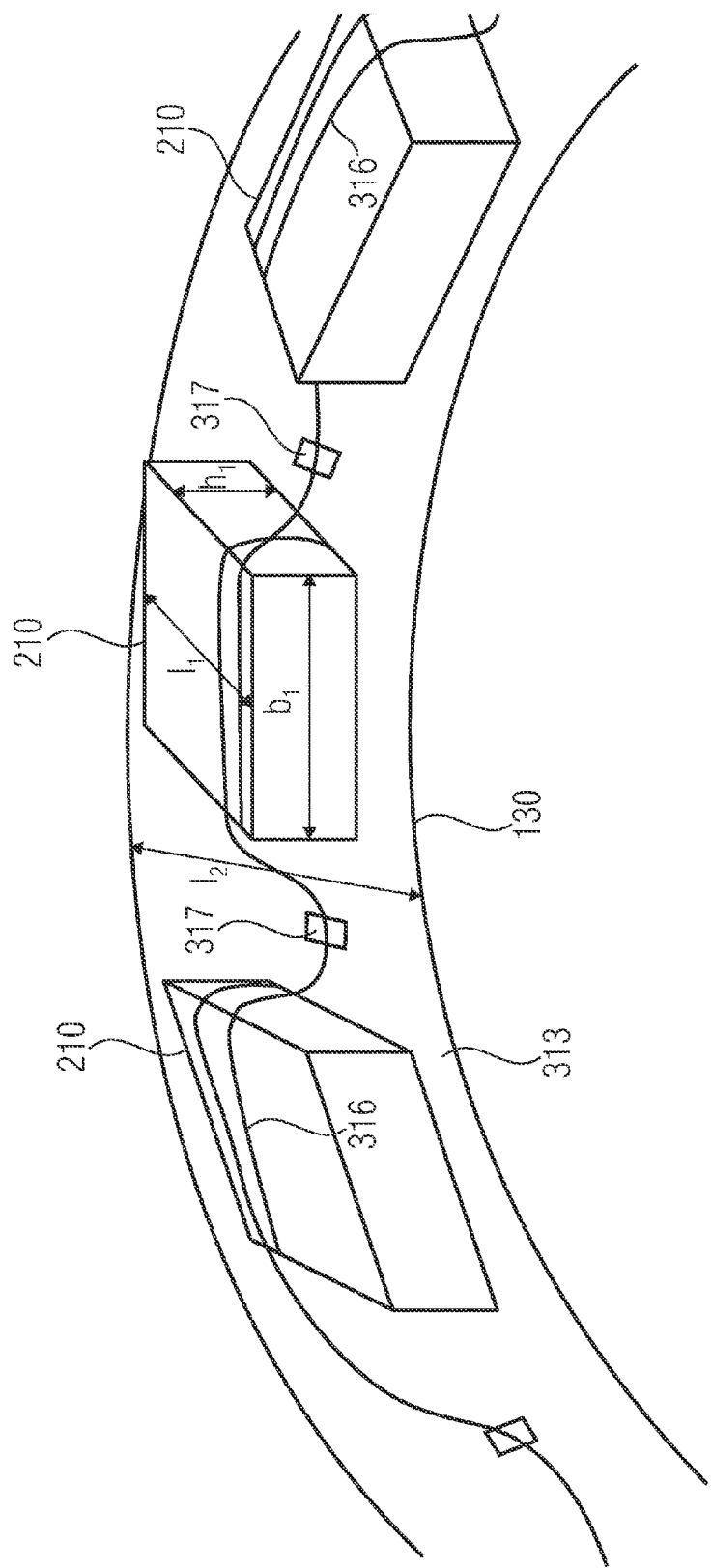
FIG. 3*b* shows an oblique view of a sub-region of the antenna arrangement of FIG. 3*a;*

FIG. 3b shows an oblique view of a sub-region of the antenna arrangement 300 in accordance with FIG. 3a. In FIG. 3b, a sub-region of the conductor loop 313 of the transmitting antenna 130 including three compensation coils 210 arranged on the conductor loop 313 is illustrated. Each of the compensation coils 210 here have a winding 316 which is orthogonal to the transmitting antenna 130. In accordance with further embodiments, the compensation coils 210 may also comprise a plurality of windings 316. A number of windings here may be dimensioned (as described above) such that a voltage of the carrier field of the transmitting antenna 130, induced in the windings 316, equals a voltage induced in the receiving antenna 131. As also becomes evident from FIG. 3b, the compensation coils 210 are connected in series to one another. It becomes evident from FIG. 3b that the width $b_1$ of the compensation coils 210 is typically selected to be larger than the height $h_1$ of the compensation coils 210 so as to achieve a small height of the entire arrangement. In accordance with further embodiments, the height $h_1$, however, may also be selected to be greater than or equal to the width $b_1$. Additionally, it becomes evident that the width $l_2$ of the conductor loop 313 of the transmitting antenna 130 is larger than the length $l_1$ of the compensation coils 210. In accordance with some embodiments of the present invention, the dimensions of the different compensation coils 210 of the compensation means 139 may be identical or differ from one another by up to 50%, 25%, 10% or by up to 5%.

It is to be mentioned below that it is clear for a person skilled in the art that an insulation layer, such as, for example, a solder stop resist, may be arranged between the conductive trace 313 of the transmitting antenna 130 and the compensation coils 210.

In order to achieve an optimum antenna arrangement 300, it is of advantage for no voltage contributions to be caused by (parasitic) electrical fields.

This is a disadvantage of the arrangement shown in FIG. 3b, which is why the (simple linear) coils shown in FIG. 3b as compensation coils 210 which are connected in series would maybe not work very well in practice. The reason for this is the electrical field which will exist in proximity to the transmitting antenna 130 (at least in case a voltage is applied to the transmitting antenna 130). As mentioned before, when using the antenna arrangement 300 in a suitable transponder reader, there will be a voltage amplitude of about 240 volts over the transmitting antenna 130. This causes high electrical field strengths in the proximity of the transmitting antenna 130.

The compensation means 139 which is placed in proximity to the transmitting (i.e. carrier emitting) coil or transmitting antenna 130 has an unavoidable capacitive coupling to the transmitting antenna 130.

Figure 3C:
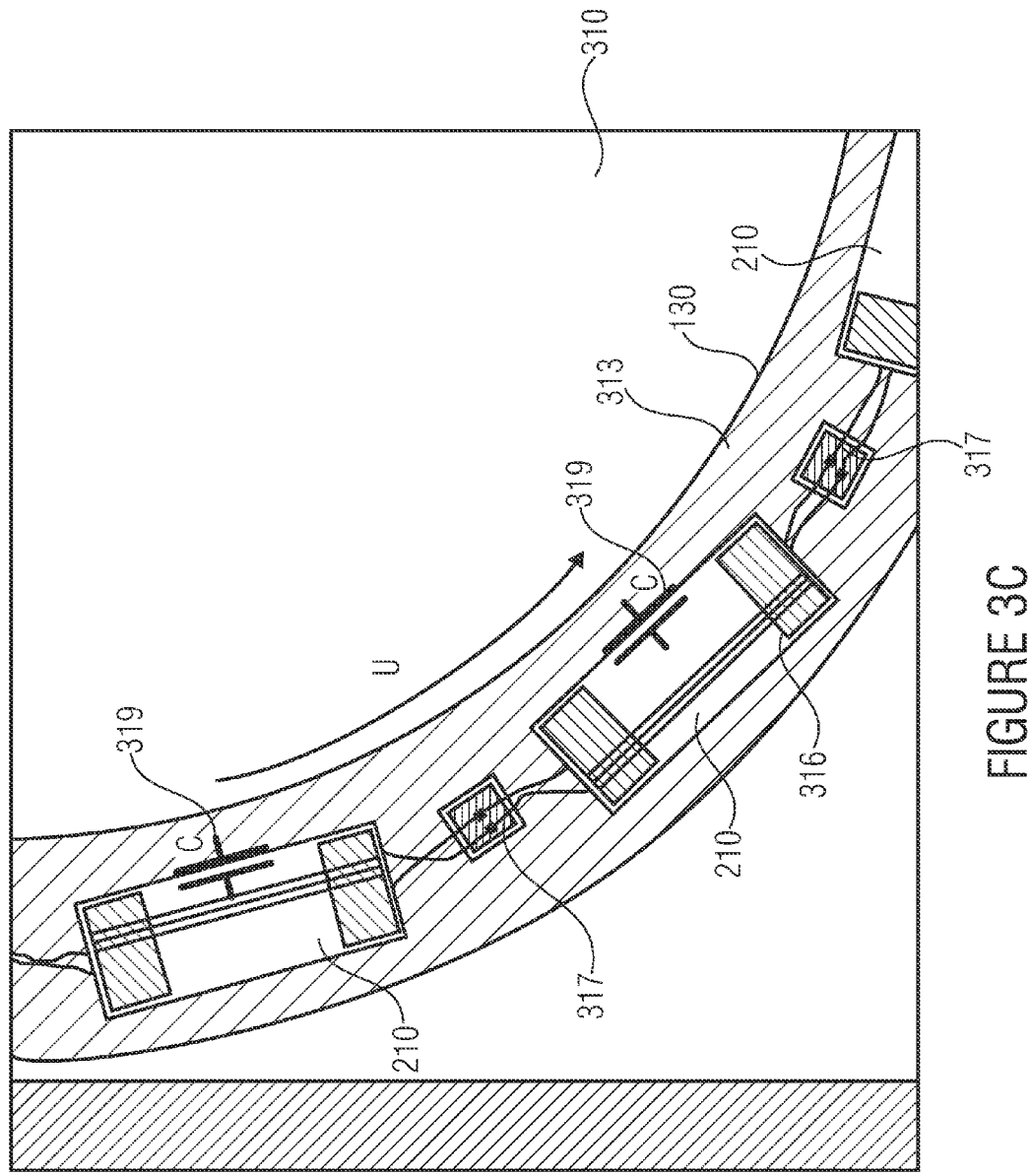
FIG. 3*c* shows a top view of a sub-region of the antenna arrangement of FIG. 3*a* for illustrating parasitic capacitances.
Figure 3D:
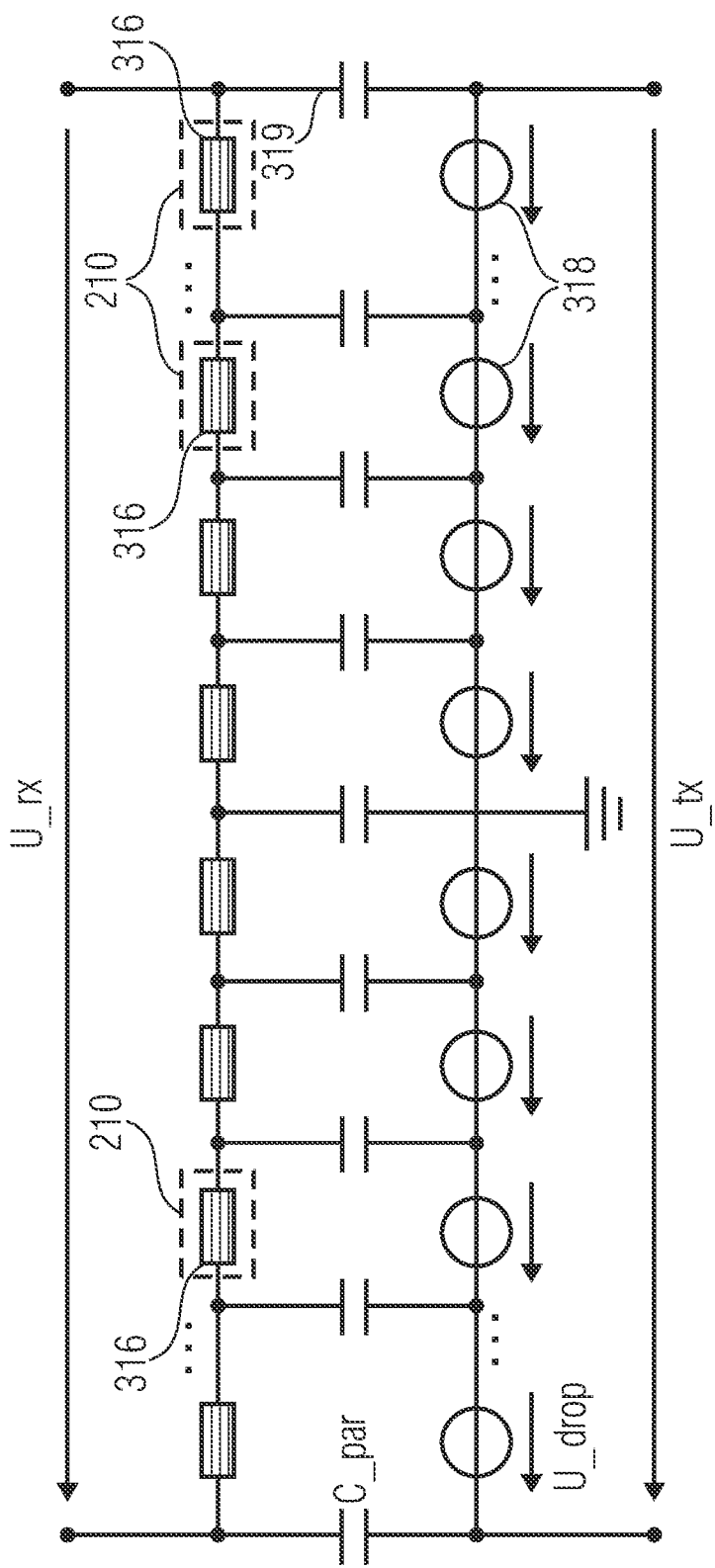
FIG. 3*d* shows an equivalent circuit diagram for the antenna arrangement of FIG. 3*a;*

FIG. 3c illustrates the parasitic capacitances 319 between the compensation coils 210 and the field-generating transmitting antenna 130. The unwanted carrier signal of the transmitting antenna 130 is coupled into the receiving antenna coil (into the receiving antenna 131) via this parasitic path. By taking a look at the equivalent circuit shown in FIG. 3d, the effect of the parasitic capacitances 319 becomes clear. The electrical potential of the transmitting antenna 130 exhibits a linear distribution along the coil wire (along the conductor loop 313). In an equivalent circuit, this may be modeled by a plurality of voltage sources 318 connected in series. The overall voltage $U_{tx}$ has an amplitude of, exemplarily, 240 volts. However, at every position where a compensation coil 210 is positioned, there is a capacitance 319 in the equivalent circuit. More precisely, when a compensation coil 210 ends, a capacitance 319 may form between the corresponding voltage sources 318 and the compensation coil 210. In other words, this capacitance 319 is connected between a voltage source 318 and the compensation coil 210. It becomes evident from the result shown in FIG. 3d that all the voltages of the voltage sources 318 are added to form $U_{rx}$. This voltage $U_{rx}$ is superimposed on the transponder signal (voltage induced by a magnetic field of a transponder in the receiving antenna 131). Consequently, such an antenna would not work optimally in practice either.

In order to avoid parasitic coupling, two things may be changed. Firstly, the compensation coils 210 may be wired symmetrically and, secondly, the voltage sources 318 in the equivalent circuit can be arranged such that all the voltages are compensated.

Figure 3E:
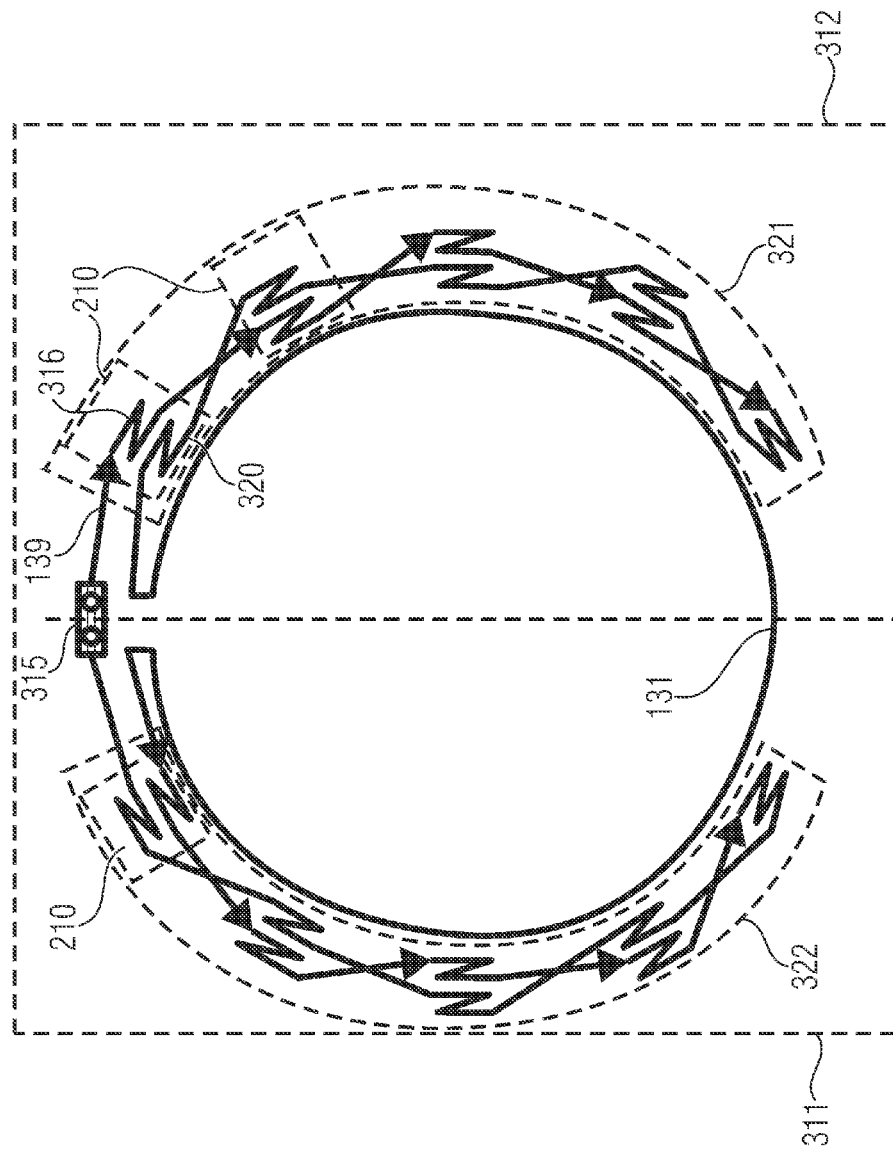
FIG. 3*e* shows a winding pattern as may be used in the antenna arrangement of FIG. 3*a* so as to avoid parasitic capacitances.

FIG. 3e shows such a symmetrical circuit arrangement designed in order for voltage pairs to be able to compensate each other. This symmetrical circuit arrangement may, in the antenna arrangement 300 in accordance with FIG. 3a, be applied to compensate the parasitic electrical capacitances generated by the compensation coils 210. In the example shown in FIG. 3e, windings of the compensation coils 210 are divided into two—advantageously similar—parts. These two parts should (nearly) exhibit the same parasitic electrical coupling and good magnetic coupling to the transmitting antenna 130.

Close magnetic coupling between the two parts (windings) of the compensation coils 210 is not mandatory, but may be of advantage for another embodiment of the present invention.

In other words, the compensation coils 210 may, in addition to the windings 316 (shown already in FIG. 3b), comprise one or several further windings 320 which are arranged on the compensation coils 210 such that a parasitic capacitance in the first windings 316 of the compensation coils 210 is compensated by a parasitic capacitance in the second windings 320 of the compensation coils 210. Each of the compensation coils 210 here has four contacts, wherein these four contacts are wired to the two parts (the first winding(s) 316 and the second winding(s) 320) of the compensation coils 210, as is shown in FIG. 3e. The first section of the entire receiving antenna (i.e. the inductive receiving antenna 131) is positioned as an inner receiving winding (as an inner receiving antenna 131) (thereby making it clear for a person skilled in the art that the receiving antenna 131 may also comprise more than one winding, followed by an appropriate dimension of the compensation coils 210). The second section of the entire receiving antenna (the compensation means 319) consists, among other things, of the compensation coils 210. The connection terminal 315 for the entire receiving antenna (formed of the receiving antenna 131 and the compensation means 319) is shown at the top of FIG. 3e.

The strictly symmetrical setup which has already been described referring to FIG. 3a also becomes evident from the illustration shown in FIG. 3e, where, in contrast to FIG. 3a, five compensation coils 210 are associated to each half of the transmitting antenna 130, whereas in FIG. 3a six compensation coils were associated to each half (both the first half 310 and the second half 312) of the transmitting antenna 130. In FIG. 3e, the transmitting antenna 130 is not illustrated for reasons of clarity. However, it is clear from the above description that the compensation coils 210 are arranged on a coil wire or a conductor loop 313 of the transmitting antenna 130 or are arranged at least in direct proximity to the transmitting antenna 130 and exemplarily enclose the coil area 213 of the transmitting antenna 130. The symmetrical setup is, as has been described before, characterized by the fact that numbers of windings of the compensation coils 210 are identical, additionally dimensions of the compensation coils 210 are identical and distances of the compensation coils 210 to one another are identical. Furthermore, the symmetrical setup is characterized by the fact that the compensation means 139 comprises a first sub-circuit 321 and a second sub-circuit 322. The first sub-circuit 321 here is connected in series upstream of the receiving antenna 131. The second sub-circuit 322 here is connected in series downstream of the receiving antenna 131. Each of the compensation coils 210 here may be associated to exactly one of the two sub-circuits. In the embodiment shown in FIG. 3e, compensation coils arranged along the first half 311 of the transmitting antenna 130 are associated to the first sub-circuit 321 and compensation coils 210 arranged along the second half 312 of the transmitting antenna 130 are associated to the second sub-circuit 322.

Subsequently, the first windings 316 of the compensation coils 210 are also referred to as the first part and the windings 320 of the compensation coils 210 referred to as the second part.

The compensation coils 210 are wired as follows: it starts with the first part (the windings 316, when similar parts are used: the first half) of the compensation coils 210 of the right hand (of the first sub-circuit 321), wired from top to bottom. Then the second part (the windings 320, when using similar parts: the second half) of the right-hand compensation coils 210 (of the compensation coils 210 of the first sub-circuit 321) is wired from bottom to top. Before wiring the left-hand side (the second sub-circuit 322) in the same manner, the receiving winding (the receiving antenna 131) is connected therebetween so as to maintain symmetry.

Figure 3F:
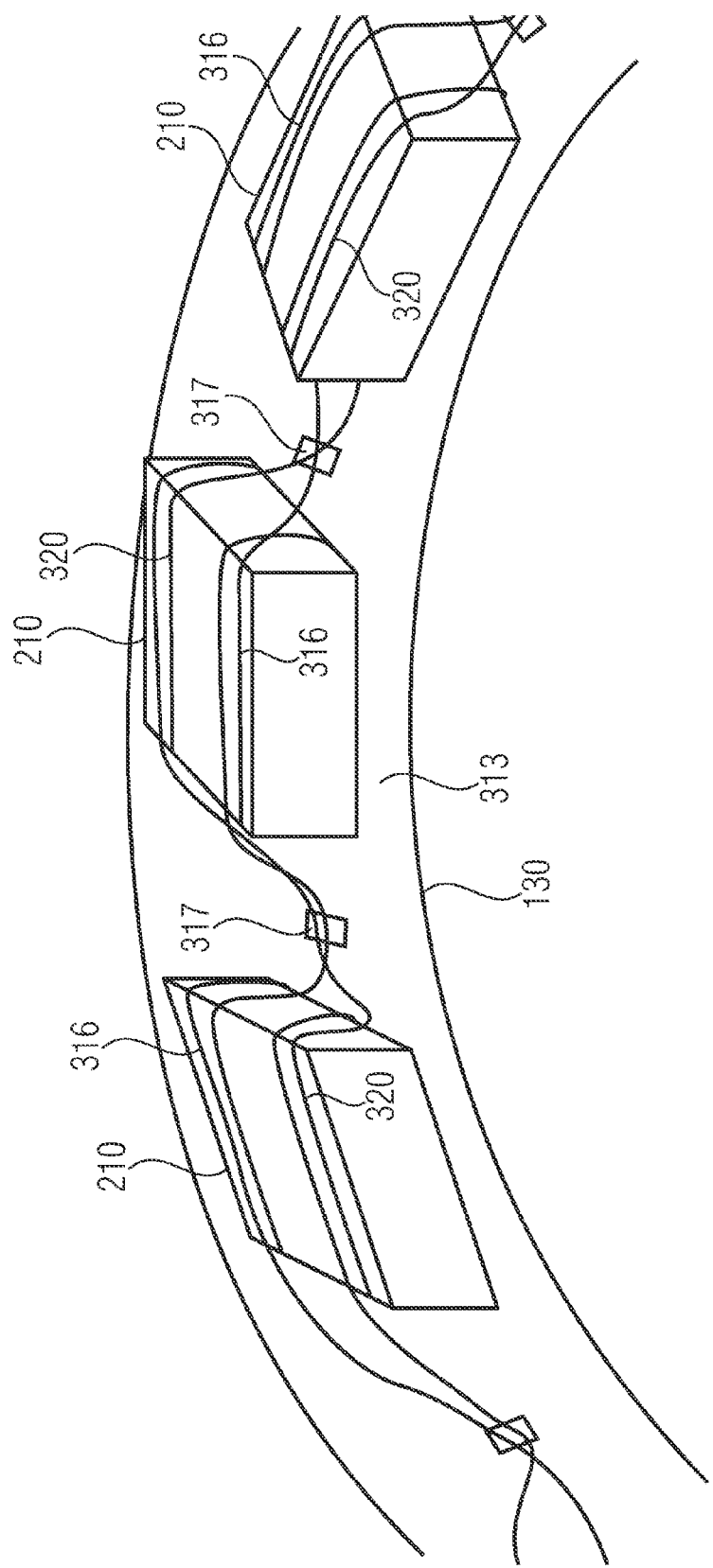
FIG. 3*f* shows an oblique view of the sub-region of FIG. 3*b* making use of the winding pattern of FIG. 3*e;*

FIG. 3f shows the sub-region of FIG. 3b including this improved layout, wherein each of the compensation coils 210 comprises, in addition to the winding(s) 316, one or several further winding(s) 320 for compensating the parasitic capacitances 319.

Figure 3G:
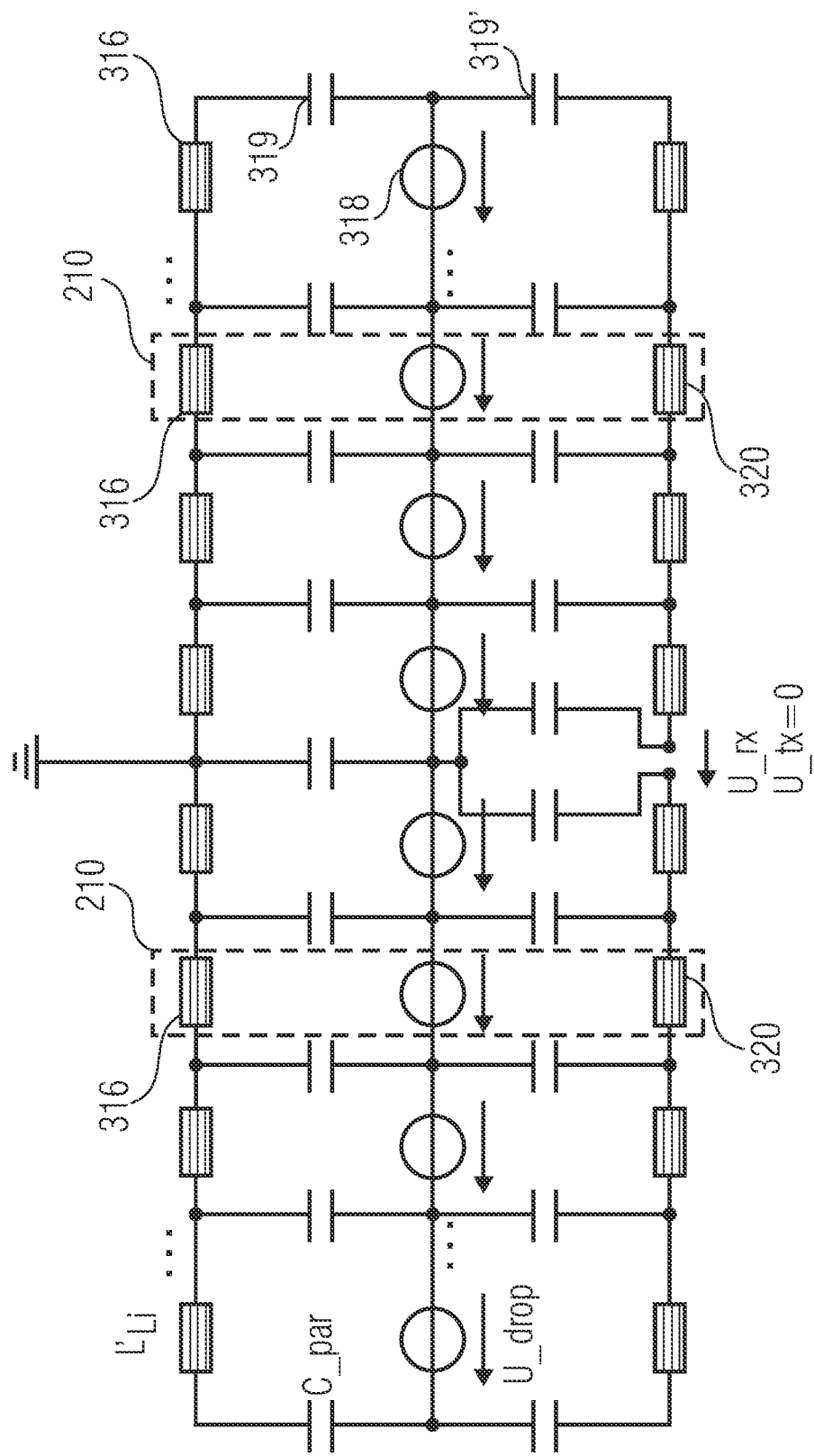
FIG. 3*g* shows an equivalent circuit diagram of the antenna arrangement of FIG. 3*a* making use of the winding pattern of FIG. 3*e* so as to avoid parasitic capacitances.

The equivalent circuit of this is illustrated in FIG. 3g. The separation of the compensation coils 210 (into windings 316 and opposite windings 320) and the way they are wired ensures that every voltage source 318 generates a positive and a negative value. Thus, the parasitic voltage sources are compensated at least to a large extent. There is—for practical use—no more (or only negligible) influence. In other words, a compensation coil 210 generates a parasitic capacitance 319 with its winding(s) 316 and a parasitic capacitance 319' with its winding(s) 320, which both generate a voltage drop. However, due to the opposite winding of the winding(s) 316 and the winding(s) 320, these voltage drops cancel each other out (at least to a large extent). In other words, each of the compensation coils 210 comprises at least a second winding 320 which is wound in the opposite direction to its respective first winding 316 such that a voltage generated by a parasitic electrical field of the transmitting antenna 130 in the first winding 316 is opposite to a voltage generated by the parasitic electrical field of the transmitting antenna 130 in the second winding 320.

Measurements with the presented antenna structure have shown that a carrier suppression of 52 dB can be achieved. Together with a ceramic filter, a signal-to-carrier ratio of about 0 dB is possible, which is a good value. The bandwidth of the receiver coil is more than 300 kHz.

t was shown, that a transponder signal could not be received in a medical application according the presented example using a conventional antenna coil. Existing solutions according to the state of the art have been presented and discussed. They also do not meet the requirements of the application in consideration. An antenna arrangement according to the invention is disclosed which enables receiving the transponder signal under the conditions of the system in consideration. Disturbing influences caused by carrier transmitting are compensated using a compensation coil which—in one embodiment—is particularly orientated orthogonal to the receiving coil. In further disclosed embodiments, the compensation coil is modified and divided in several sections and parts. Good results are obtained by using a plurality of symmetrically built compensation coils which are wired in such a manner that disturbing voltages—which are coupled in the receiving coil/antenna by the typically nearby positioned transmission coil—can be suppressed to a large extent. Therefore, sufficient SNR and SCR values can be obtained. Because of the decoupling of receiving and transmitting coils, a broadband transponder signal receiving is possible. Signal processing in the reader becomes easier. The antenna structure according to embodiments of the invention allows transmitting high magnetic field strength and at the same time receiving a small transponder signal with the needed bandwidth and data rates. Instead of conventional solutions a transponder could be read in every position in front of the antenna structure. In comparison to other solutions, the size of the antenna structure does not have to be enlarged.

Embodiments of the present invention can receive a weak transponder signal without disturbing influences by the carrier signal emitted by the reader. Broad-band reception of the transponder signal becomes possible by magnetic decoupling between the field-generating coil (of the transmitting antenna 130) and the receiving coil (the receiving antenna 131). Signal processing in a reader (exemplarily in a transponder reader in which an antenna arrangement in accordance with one embodiment of the present invention is applied) is made considerably easier by this. Finally, it is possible to increase the read range of the transponder reader considerably. By the special arrangement of the coils, it is possible (in particular compared to the examples shown in FIGS. 10 and 12) to read out the transponder at any position, in contrast to existing setups.

The principle including a compensation winding (of the compensation means 319) of canceling out the carrier field may also be achieved by a modified shape of the coils (the compensation coils 210). Compensation means 139 in the form of a wound ring core which is introduced into the antenna resonant circuit would be conceivable, for example.

Figure 4:
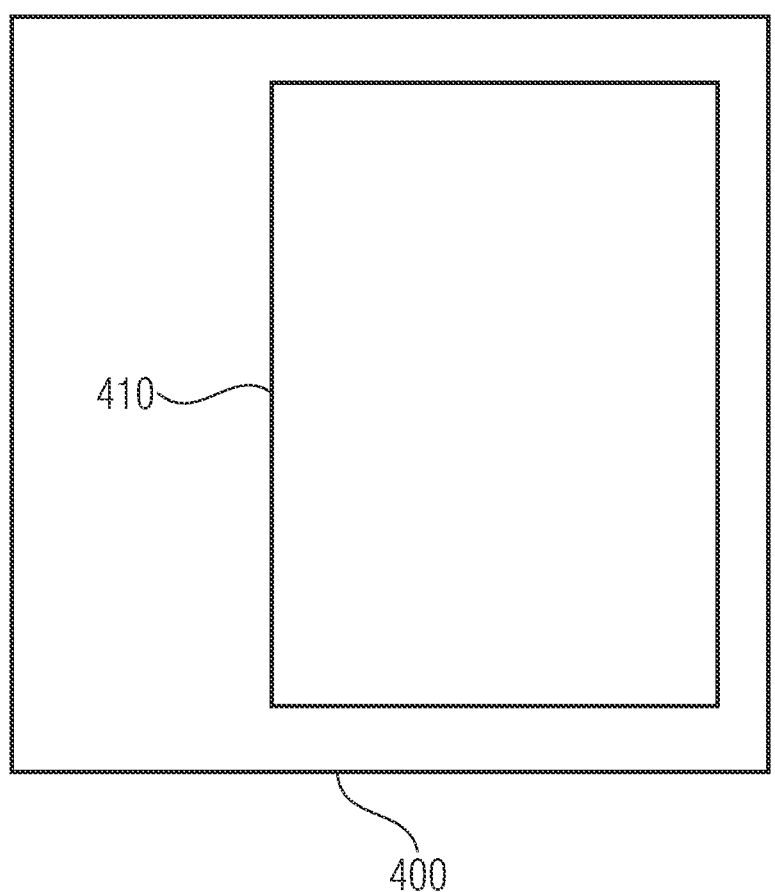
FIG. 4 shows a block circuit diagram of a transponder reader in accordance with an embodiment of the present invention.
Figure 5:
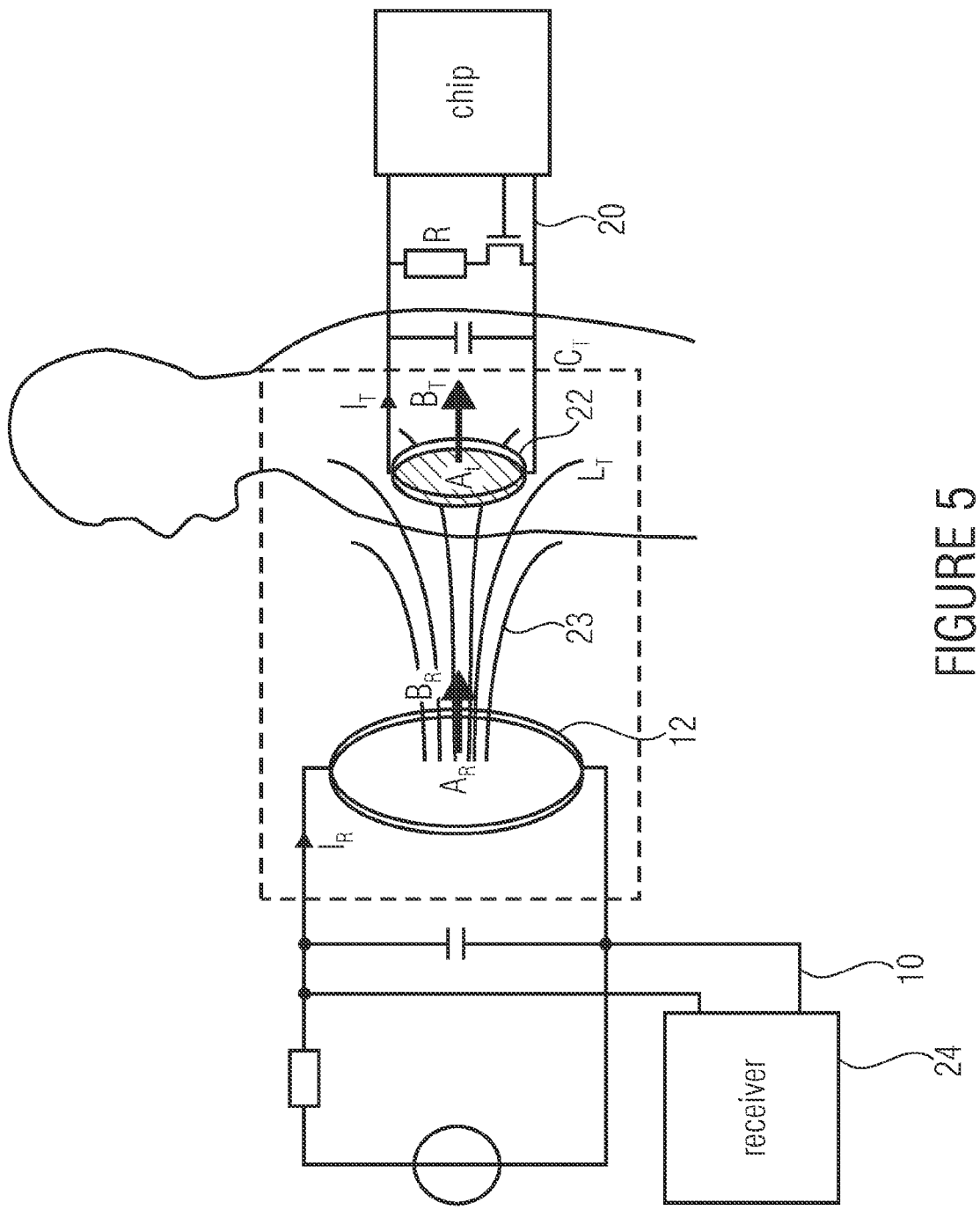
FIG. 5 shows a block circuit diagram of a sensor transponder system.
Figure 6:
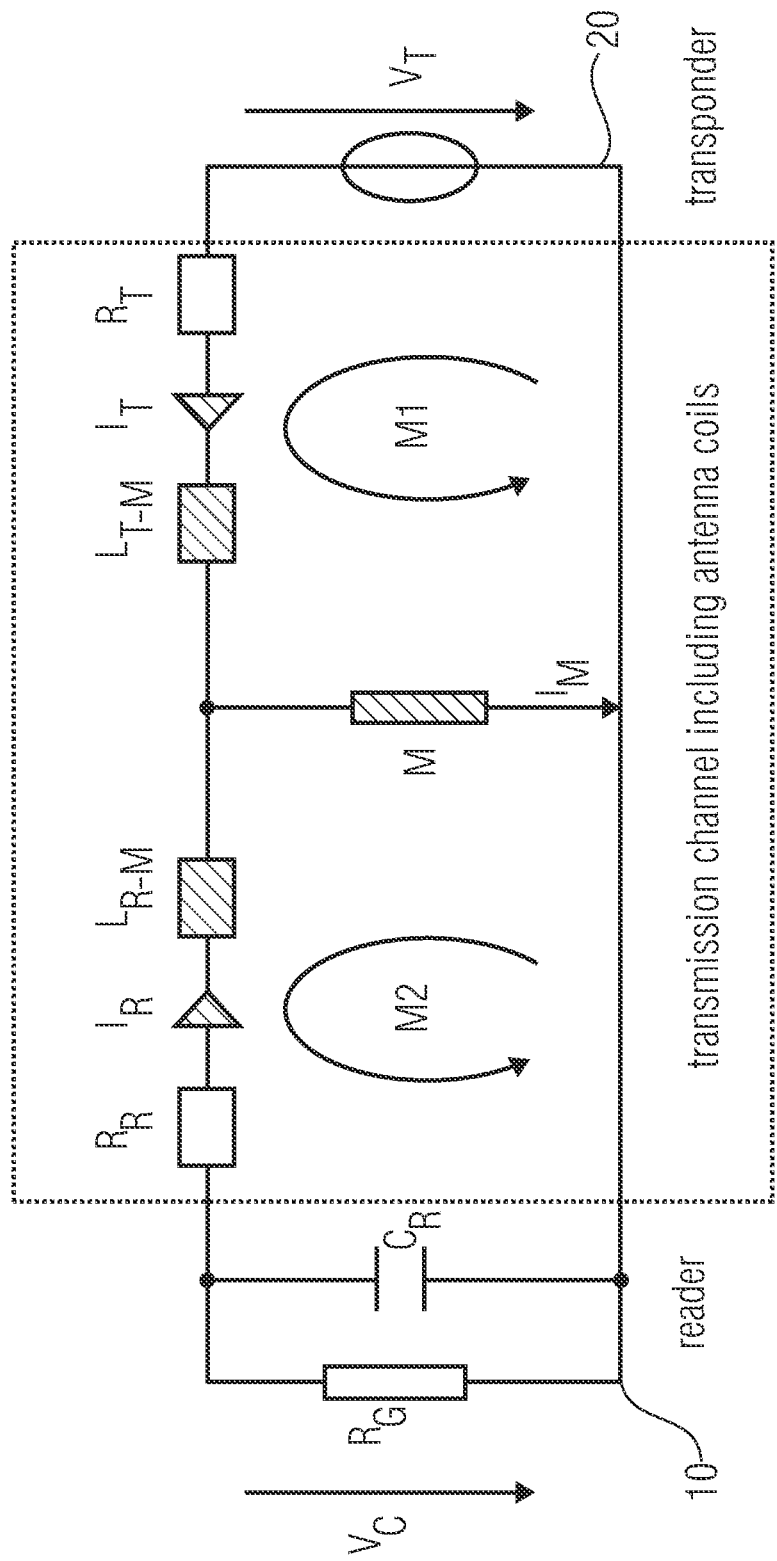
FIG. 6 shows an equivalent circuit diagram of the sensor transponder system of FIG. 5.
Figure 7:
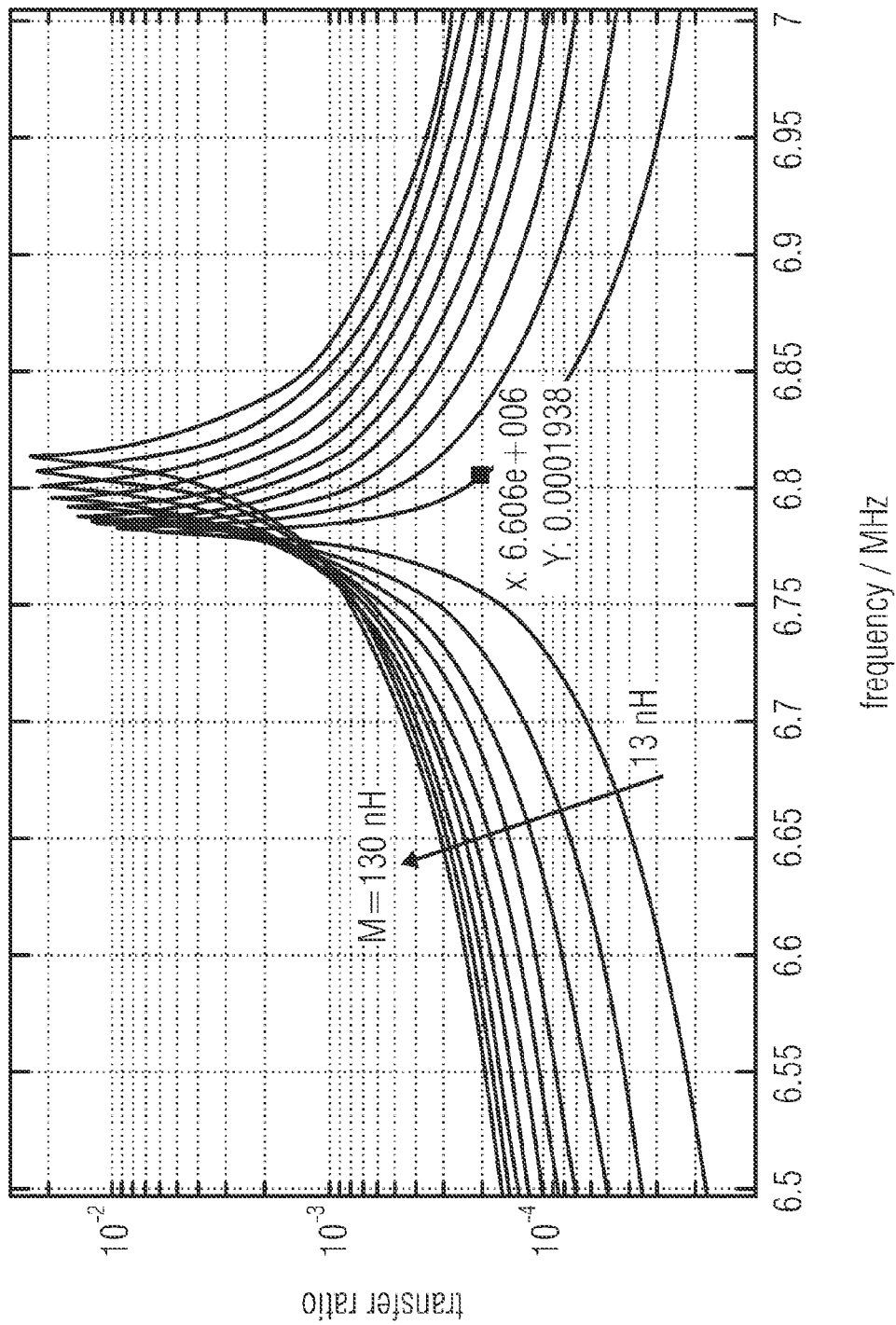
FIG. 7 shows a diagram of a transfer function of the equivalent circuit diagram shown in FIG. 6.
Figure 8:
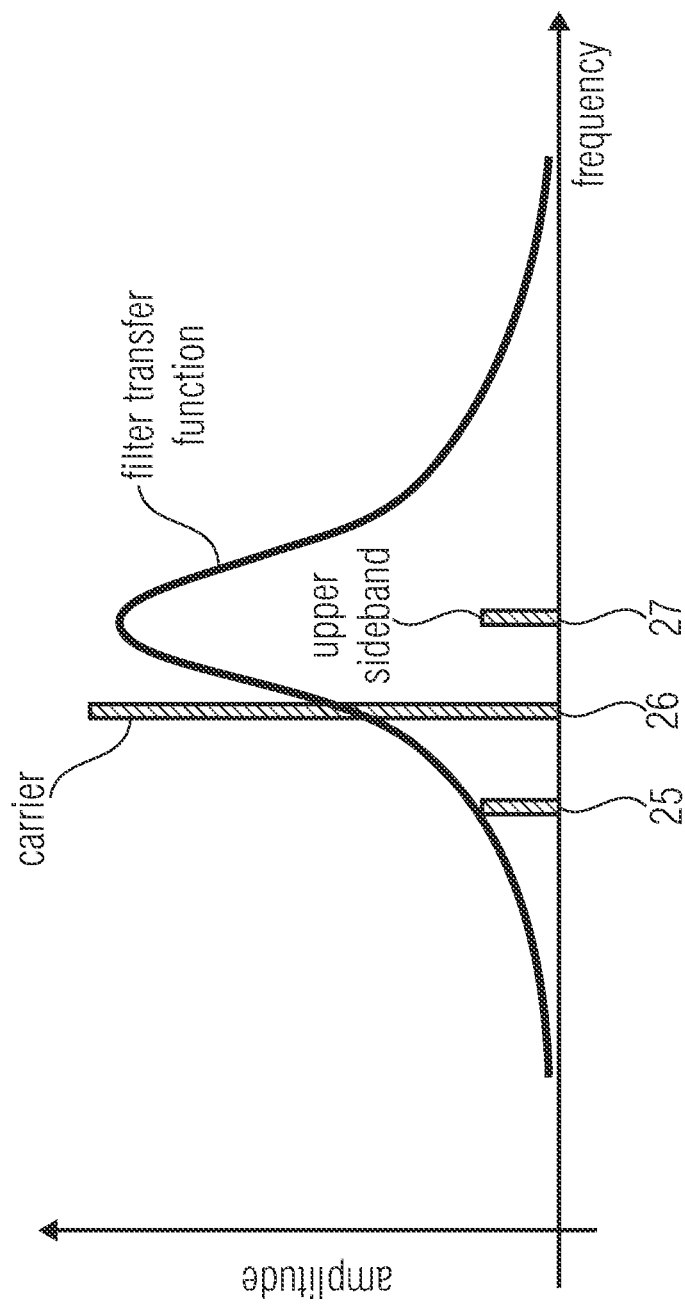
FIG. 8 shows a diagram for utilizing a filter for filtering a carrier in a wireless transmission system.
Figure 9:
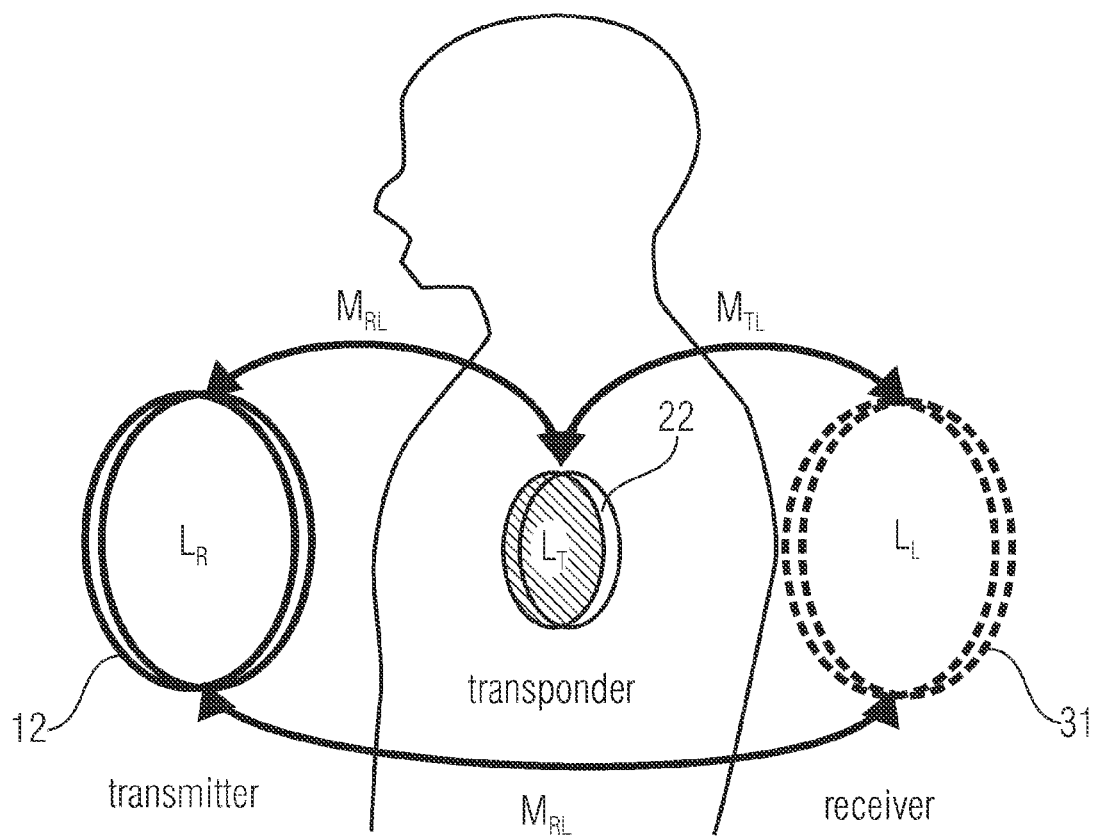
FIG. 9 shows a schematic illustration of a sensor transponder system including spatial separation of transmitting and receiving coils.

FIG. 4 shows a block diagram of a transponder reader 400 in accordance with an embodiment of the present invention. The transponder reader 400 comprises an antenna arrangement 410. The antenna arrangement 410 may exemplarily be the antenna arrangement 100 in accordance with FIG. 1, the antenna arrangement 200 in accordance with FIG. 2, the antenna arrangement 300 in accordance with FIG. 3a or another antenna arrangement in accordance with an embodiment of the present invention. The transponder reader 400 including the antenna arrangement 410 may, in contrast to existing transponder readers which do not exhibit carrier suppression by compensation means as has been described making reference to embodiments of the present invention, exhibit an increased read range and, in particular, higher sensitivity when receiving transponder signals. The transponder reader may exemplarily be an RFID reader, an NFC reader or a reader for any wireless transmission method which is based on inductive transmission.

The advantages and features of embodiments of the present invention compared to the known art are to be summarized below.

This invention discloses the analysis and optimization of carrier suppression methods in order to improve the performance of such systems. It is shown that conventional approaches are not suitable for this application. A novel antenna structure in the form of conductive loops, in particular coils, is illustrated which allows transmitting data as well as power so as to supply the electronic circuits of a passive sensor transponder over a distance of up to 40 cm (and more). Measurements show increased carrier suppression, in one embodiment of about 52 dB.

It was shown, that a transponder signal could not be received in a medical application according the presented example using a conventional antenna coil. Existing solutions according to the known art have been presented and discussed. Neither do they meet the requirements of the application in consideration. An antenna arrangement according to the invention is disclosed which enables receiving the transponder signal under the conditions of the system in consideration. Disturbing influences caused by carrier transmission are compensated by using a compensation coil which—in one embodiment—is particularly orientated orthogonal to the receiving coil. In further disclosed embodiments, the compensation coil is modified and divided in several sections and parts. Good results are obtained by using a plurality of symmetrically built compensation coils which are wired in such a manner that disturbing voltages—which are coupled in the receiving coil/antenna by the typically nearby positioned transmission coil—can be suppressed to a large extent.

Therefore, sufficient SNR and SCR values can be obtained. Because of the decoupling of receiving and transmitting coil, broadband transponder signal receiving is possible. Signal processing in the reader becomes easier. The antenna structure according to the invention allows transmitting high magnetic field strength and at the same time receiving a small transponder signal with the needed bandwidth and data rates. Instead of conventional solutions, a transponder could be read in every position in front of the antenna structure. In comparison to other solutions, the size of the antenna structure does not have to be enlarged.

Embodiments of the present invention provide an antenna arrangement which comprises at least one transmitting antenna loop or transmitting antenna coil and at least one receiving antenna loop or receiving antenna coil, wherein the at least one transmitting antenna loop or transmitting antenna coil and the at least one receiving antenna loop or receiving antenna coil are positioned in proximity to each other, characterized by at least one compensation antenna loop or compensation antenna coil which is provided as part of the at least one receiving antenna loop, by which a signal transmitted by the at least one transmitting antenna loop causes at least one compensation signal in the at least one compensation antenna loop such that direct transmission between the at least one transmitting antenna loop and the at least one receiving antenna loop is suppressible at least to a large extent.

Further embodiments of the present invention are characterized by an orthogonal orientation of the at least one compensation antenna loop or compensation antenna coil with respect to the at least one transmitting antenna loop and the at least one receiving antenna loop.

Further embodiments of the present invention are characterized by a symmetrical design of the at least one compensation loop or compensation coil.

Further embodiments of the present invention are characterized by the fact that antenna coils are inserted into the receiving loop or receiving coil, whereby the compensation coils comprise two separate windings which are connected in such an orientation which allows compensation of parasitic electrical fields generated by the transmitting loop or transmitting coil.

Embodiments of the present invention may be employed in any transponder system. Embodiments of the present invention are interesting in particular for sensor transponder systems. Sensor transponders exhibit a higher current consumption than simple ID (identification) transponders. Thus, high-quality antennas may be used for field generation. However, the relatively broad-band transponder signal can then no longer be received. Using the antenna arrangement presented here, however, broad-band reception will also be possible.

Additionally, embodiments of the present invention may be employed in all inductively operating apparatuses in which a receiver is located and an electromagnetic alternating field is generated.

In summary, embodiments of the present invention provide a transmitting/receiving antenna for transponder readers including carrier suppression. A core idea of embodiments of the present invention are measures for decoupling the usually spatially neighboring transmitting and receiving conductor loops in a transponder reader (referred to by experts as reader).

Since the transmitting/receiving antennas used for such readers are to be set up to be geometrically as small as possible or compact, embodiments described here concentrate on a planar or flat realization.

Knowing that, on the one hand, the magnetic transmitting field, in the proximity of the transmitting loop, is radially symmetrical around same and only forms an axial component at a greater distance and that, on the other hand, the data receiving field, in the area of the flat antenna setup, comprises, practically exclusively, an axial component, a compensation circuit consisting of, among other things, several coils may be inserted into the receiving conductor loop of the reader antenna arrangement such that the voltages induced by the radial magnetic transmitting field cancel out the directly received transmitting signal. Further measures relating to circuit technology reduce interferences coupled into the receiving conductor loop by the electrical transmitting field.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

The invention claimed is:

1. An antenna arrangement comprising:
   an inductive transmitting antenna comprising a main radiating axis;
   an inductive receiving antenna comprising a main receiving axis located in the main radiating axis of the inductive transmitting antenna; and
   an inductive compensator which is electrically connected in series to the inductive receiving antenna and located in a first plane which intersects a second plane, the main receiving axis of the inductive receiving antenna being normal to the second plane; wherein the inductive compensator extends, at least in an area of a conductor of the inductive transmitting antenna, along the conductor.

2. The antenna arrangement in accordance with claim 1, wherein the first plane is orthogonal to the second plane.

3. The antenna arrangement in accordance with claim 1, wherein the inductive transmitting antenna is located in the second plane and the inductive receiving antenna is located in the second plane or in a third plane which is parallel to the second plane.

4. The antenna arrangement in accordance with claim 1, wherein the inductive receiving antenna and the inductive transmitting antenna overlap at least partly.

5. An antenna arrangement comprising:
an inductive transmitting antenna comprising a main radiating axis;
an inductive receiving antenna comprising a main receiving axis located in the main radiating axis of the inductive transmitting antenna; and
an inductive compensator which is electrically connected in series to the inductive receiving antenna and located in a first plane which intersects a second plane, the main receiving axis of the inductive receiving antenna being normal to the second plane; wherein
the inductive transmitting antenna encloses the inductive receiving antenna.

6. The antenna arrangement in accordance with claim 1, wherein the inductive compensator comprises a plurality of coils connected in series, each comprising at least one first winding, wherein the windings of the plurality of windings are located in the first plane, and wherein the plurality of coils extend along the conductor of the inductive transmitting antenna.

7. The antenna arrangement in accordance with claim 6, wherein the inductive compensator comprises a first sub-circuit and a second sub-circuit, the first sub-circuit being connected in series upstream of the inductive receiving antenna and the second sub-circuit being connected in series downstream of the inductive receiving antenna, and wherein each of the coils of the plurality of coils is associated to either the first sub-circuit or the second sub-circuit.

8. The antenna arrangement in accordance with claim 7, wherein coils of the plurality of coils which are associated to the first sub-circuit are arranged along a first half of the conductor and coils of the plurality of coils which are associated to the second sub-circuit are arranged along a second half of the conductor of the inductive transmitting antenna.

9. The antenna arrangement in accordance with claim 8, wherein an arrangement of the coils along the first half of the conductor of the inductive transmitting antenna is symmetrical to an arrangement of the coils along the second half of the conductor of the inductive transmitting antenna.

10. The antenna arrangement in accordance with claim 1, wherein at least one of the coils of the plurality of coils comprises at least one second winding which is wound in the opposite direction to its respective first winding such that a voltage generated by a parasitic electrical field of the transmitting coil in the first winding is opposite to a voltage generated by the parasitic electrical field of the transmitting coil in the second winding.

11. The antenna arrangement in accordance with claim 1, wherein the conductor of the transmitting coil is a first conductive trace which forms a conductor loop, and wherein the plurality of coils are surface-mountable devices arranged on the conductor loop.

12. The antenna arrangement in accordance with claim 1, wherein the inductive transmitting antenna, the inductive receiving antenna and the inductive compensator are arranged on a common substrate.

13. The antenna arrangement in accordance with claim 12, wherein the inductive compensator is arranged on a surface of the substrate.

14. The antenna arrangement in accordance with claim 12, wherein the common substrate is a printable circuit board.

15. A transponder reader comprising an antenna arrangement comprising: an inductive transmitting antenna comprising a main radiating axis; an inductive receiving antenna comprising a main receiving axis located in the main radiating axis of the inductive transmitting antenna; and an inductive compensator which is electrically connected in series to the inductive receiving antenna and located in a first plane which intersects a second plane, the main receiving axis of the inductive receiving antenna being normal to the second plane; wherein the inductive compensator extends, at least in an area of a conductor of the inductive transmitting antenna, along the conductor.

* * * * *